(12) United States Patent
Khan et al.

(10) Patent No.: US 12,254,975 B2
(45) Date of Patent: Mar. 18, 2025

(54) HEALTH DATA PROCESSING AND SYSTEM

(71) Applicant: Persivia Inc., Marlborough, MA (US)

(72) Inventors: Mansoor Khan, Shrewsbury, MA (US); Fauzia Khan, Shrewsbury, MA (US); Muhammad Kashif, Shrewsbury, MA (US)

(73) Assignee: Persivia Inc., Marlborough, MA (US)

( * ) Notice: Subject to any disclaimer, the term of this patent is extended or adjusted under 35 U.S.C. 154(b) by 310 days.

(21) Appl. No.: 17/196,976

(22) Filed: Mar. 9, 2021

(65) Prior Publication Data

US 2021/0313049 A1 Oct. 7, 2021

Related U.S. Application Data

(60) Provisional application No. 62/987,749, filed on Mar. 10, 2020.

(51) Int. Cl.
*G16H 40/20* (2018.01)
*G06F 9/451* (2018.01)
(Continued)

(52) U.S. Cl.
CPC ............ *G16H 40/20* (2018.01); *G06F 9/451* (2018.02); *G06N 20/00* (2019.01); *G16H 10/60* (2018.01)

(58) Field of Classification Search
CPC ........ G16H 40/20; G16H 15/00; G16H 50/70; G16H 10/60; G06F 40/186; G06F 16/275; G06F 3/0482; G06F 9/451; G06N 20/00
See application file for complete search history.

(56) References Cited

U.S. PATENT DOCUMENTS 9,247,522 B1 * 1/2016 Chen .................... H04W 4/029
11,126,696 B1 * 9/2021 Srivastava ............. G16H 40/20
(Continued)

OTHER PUBLICATIONS

Faiola, Anthony J. A Ubiquitous Situation-Aware Data Visualization Dashboard to Reduce ICU Clinician Cognitive Load. IEEE 17th International Conference on e-Health Networking, Applications and Services (Healthcom): Short and Demo Papers. 2015 (Year: 2015).*
(Continued)

*Primary Examiner* — Christopher L Gilligan
*Assistant Examiner* — Tristan Isaac Evans
(74) *Attorney, Agent, or Firm* — Wolf, Greenfield & Sacks, P.C.

(57) ABSTRACT

Provided are methods for generating a workflow of a healthcare professional and methods of generating graphical user interfaces (GUI) that display the workflow of the healthcare professional. A workflow of a healthcare professional may include an ordered list of healthcare events associated with the healthcare professional. Each healthcare event in the ordered list may request the attention of the healthcare professional or may provide an indication that the healthcare professional should complete some associated work. Healthcare events may include tasks for the healthcare professional, alerts such as new lab results for patients, scheduled appointments with patients, or appointment requests from patients. The workflow may provide a healthcare professional with, in one user interface all, substantially all, or a majority of the healthcare events that the healthcare professional should be aware to perform their job.

19 Claims, 33 Drawing Sheets

(51) Int. Cl.
*G06N 20/00* (2019.01)
*G16H 10/60* (2018.01)

(56) References Cited

U.S. PATENT DOCUMENTS

| | | | | |
|---|---|---|---|---|
| 12,112,124 | B1* | 10/2024 | Boliek | G06F 40/186 |
| 2004/0122708 | A1 | 6/2004 | Avinash et al. | |
| 2007/0168225 | A1* | 7/2007 | Haider | G16H 10/20 |
| | | | | 128/920 |
| 2007/0179361 | A1* | 8/2007 | Brown | A61B 5/411 |
| | | | | 600/300 |
| 2010/0131292 | A1* | 5/2010 | Hawkins | G06Q 10/06 |
| | | | | 705/3 |
| 2012/0004925 | A1 | 1/2012 | Braverman et al. | |
| 2012/0065987 | A1* | 3/2012 | Farooq | G16H 50/70 |
| | | | | 705/2 |
| 2012/0226508 | A1* | 9/2012 | Sievenpiper | G16H 40/20 |
| | | | | 705/2 |
| 2012/0303388 | A1 | 11/2012 | Vishnubhatla et al. | |
| 2015/0046181 | A1 | 2/2015 | Adjaoute | |
| 2015/0106119 | A1* | 4/2015 | McCafferty | G16H 40/20 |
| | | | | 705/3 |
| 2016/0239778 | A1* | 8/2016 | Suneja | G06Q 10/06316 |
| 2018/0349556 | A1* | 12/2018 | Owen | G16H 15/00 |
| 2020/0273581 | A1* | 8/2020 | Wolf | G16H 40/63 |
| 2020/0303069 | A1* | 9/2020 | Mulligan | G06N 5/02 |

OTHER PUBLICATIONS

Wright, Adam. A four-phase model of the evolution of clinical decision support architectures. International Journal of Medical Informatics 77 (2008) 641-649. (Year: 2008).*

Fushman, Demner, Dina. What can natural language processing do for clinical decision support? Journal of Biomedical Informatics 42 (2009) 760-772. (Year: 2009).*

International Search Report and Written Opinion mailed May 25, 2021 in connection with International Application No. PCT/US2021/021591.

* cited by examiner

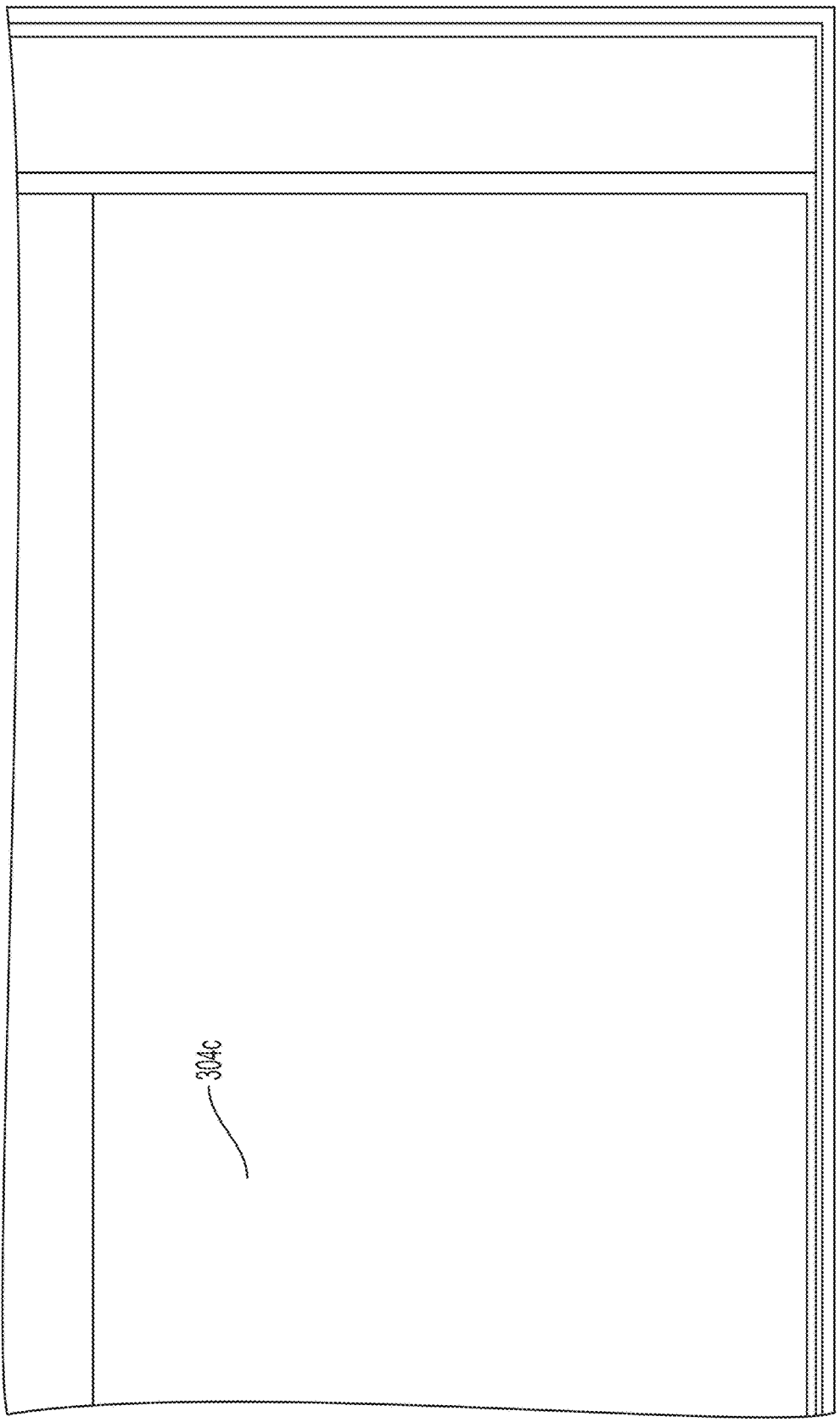

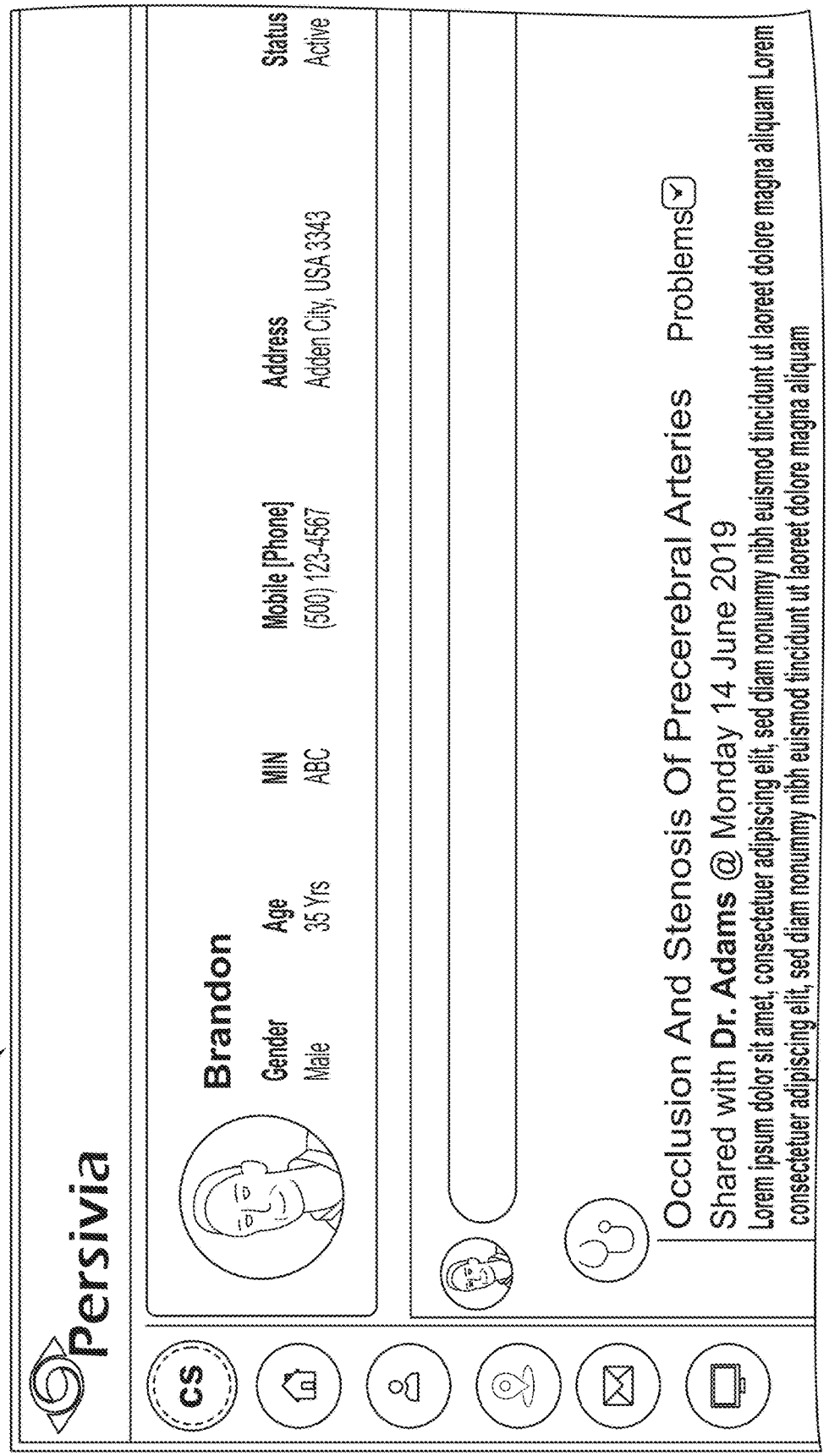

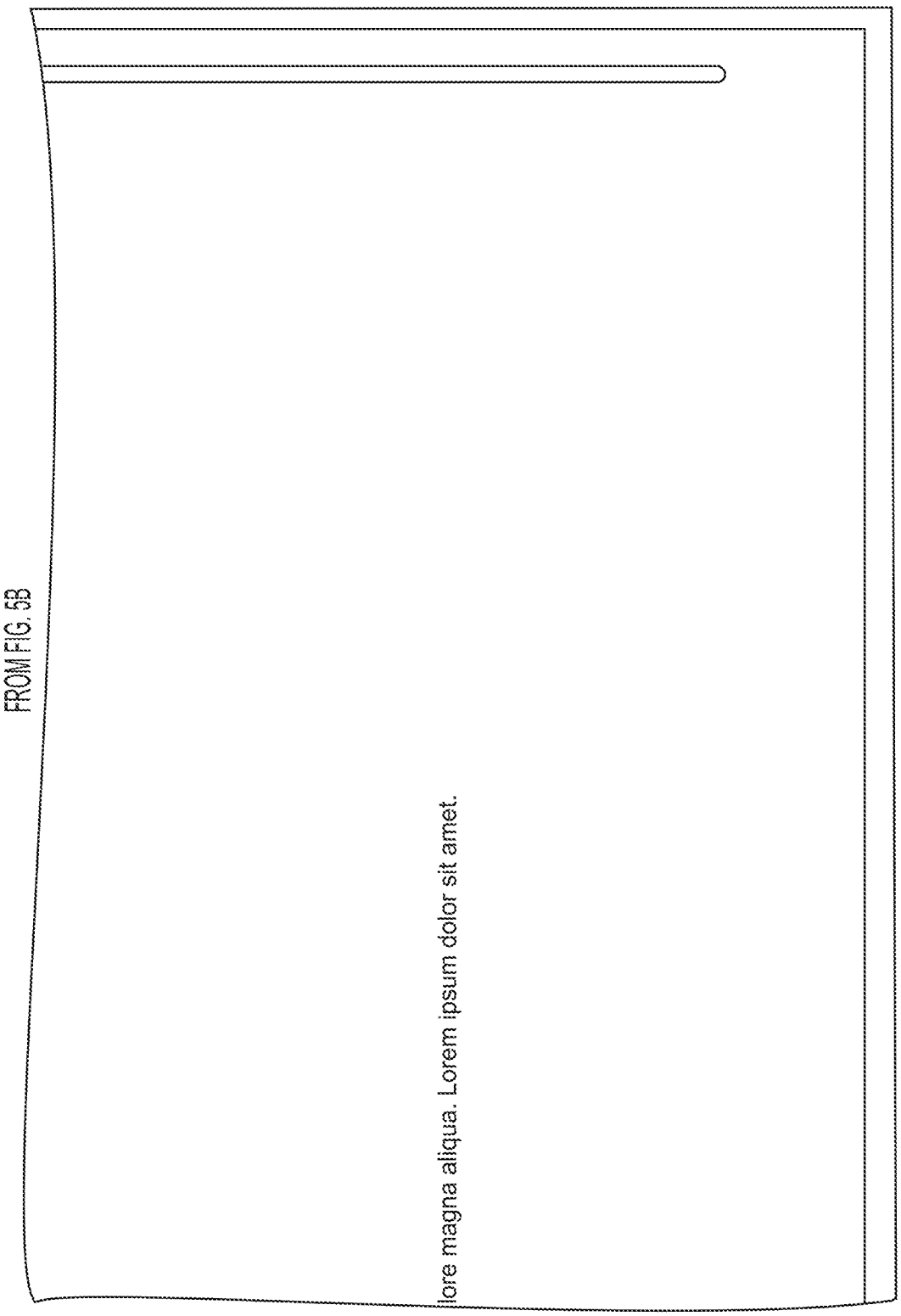

FIG. 6C

*Manage Rule: Flex Rule*

[Cancel] [Save and Close] [Reload] [Show Report]

1. • All of the conditions are met
2. Demographics [Age >= 18 yr] X
3. [Select Condition]

| | CD Variable | PE_CABG_PCI_HPC_ |
|---|---|---|
| 4. All | ▲ IVD_CAD_ICD9_ICD10_SNO_DX_ | |
| 5. Any | | |
| 6. Not all | ▲ X | |
| 7. Not any | | |
| 8. All Within | ▲ Io AA_CDC_HbA1c_Tests_CPT_ | |
| 9. Episode of Care | | |
| 10. Evaluation Date | ▲ Io PE_Blood_Urea_SNO_CPT_L | |
| | Identification | |
| | Demographics | ▲ Io AA_MPM_SerumCreatinine_CP |
| | Vital Signs | |
| | Service Event | |
| | History Of Encounters | |
| | Medical Equipment | |

FROM FIG. 9A

TO FIG. 9D

| | | |
|---|---|---|
| 11 | Allergies And Adverse Reactions ▲ | ○ D1_CBC_CPT_LOINC_SNOM |
| 12 | History Of Signs and Symptoms ▲ | ○ AA_Urinalysis_CPT_LOINC_S |
| | History Of Past Illness ▲ | |
| 13 | Problem ▲ | |
| | Medication ▲ | |
| | HDS13ASMDispense ▲ | |
| | HDS14ASMDispense ▲ | |
| | Immunization ▲ | |
| | Laboratory Panel Report ▲ | |
| | Investigation Report ▲ | |
| | Procedures and Interventions ▲ | |
| | Functional Status ▲ | |
| | Family History ▲ | |
| | Social History ▲ | |
| | Plan of Care ▲ | |
| | Patient Characteristics ▲ | |
| | Eligibility Criteria ▲ | |
| | Service line ▲ | |
| | Provider ▲ | |
| | Utilities ▲ | |
| | Days Difference ▲ | |

| Cost Type | Current Period | Previous Period | % Change | |
|---|---|---|---|---|
| Total PMPY | $11,275.93 | $12,765.92 | ⇊ | -11.67% |
| ED PMPY | $434.81 | $455.97 | ↓ | -4.64% |
| IP PMPY | $4,295.43 | $4,858.40 | ⇊ | -11.77% |
| HH PMPY | $386.38 | $597.55 | ⇊ | -35.34% |
| SNF PMPY | $768.47 | $1,003.56 | ⇊ | -23.43% |

Quality, cost, and utilization from claims compared to

| Primary Care Focused Quality | | | | |
|---|---|---|---|---|
| Metic (PCP-focused quality) | Current Period | Previous Period | % Change | |
| % Incomplete AWV | 47.70% | 52.50% | ⇊ | -9.10% |
| % Patients No PCP Visit In 6m | 11.90% | 6.70% | ↑ | 77.60% |
| % HF Patients Not Seen 3m | 95.70% | 97.90% | ↓ | -2.20% |
| % ED w/o Follow-up by 14d | 58.60% | 61.10% | ↓ | -4.10% |
| Avg. HCC | 1.20 | 1.60 | ⇊ | -25.00% |
| # of Chronic Patient(s) | 170 | 282 | ⇊ | -39.70% |

| Cost or Utilization | | | | |
|---|---|---|---|---|
| Metric (PCP-focused quality) | Current Period | Previous Period | % Change | |
| Total PMPY | $10,017.77 | $12,475.03 | ⇊ | -19.70% |
| ED PMPY | $285.26 | $392.69 | ⇊ | -27.40% |
| ED enc/1000 mem,-years | 497 | 547 | ⇊ | -9.00% |
| HH PMPY | $536.50 | $1,331.90 | ⇊ | -59.70% |
| HH enc/1000 mem,-years | 161 | 409 | ⇊ | -60.70% |
| IP PMPY | $3,186.46 | $3,556.44 | ⇊ | -10.40% |
| IP enc/1000 mem,-years | 216 | 269 | ⇊ | -19.60% |
| SNF PMPY | $461.24 | $767.97 | ⇊ | -39.90% |
| SNF enc/1000 mem,-years | Screenshot | 109 | ⇊ | -17.30% |

Manage Rule: Flex Rule

[Cancel] [Save and Close] [Reload] [Show Report]

1. • All of the conditions are met
2. Demographics [Age >= 18 yr] X
3. [Select Condition]
4. - Any of the conditions are met: X
5. , Procedures and Interventions | CD Variable PE_CABG_PCI_HPC_SNC_
6. , Problem | CD Variable PE_AMI_IVD_CAD_ICD9_ICD10_SNO_DX_CCM_
7. - Any of the conditions are not met: X
8. , Investigation Report | CD Variable AA_CDC_HbA1c_Tests_CPT_LOINC_
9. , Investigation Report | CD Variable PE_Blood_Urea_SNO_CPT_LOINC_P
10. , Investigation Report | CD Variable AA_MPM_SerumCreatinine_CPT_LOIN

TO FIG. 12B
TO FIG. 12C

| | | |
|---|---|---|
| 11 | Investigation Report | CD Variable D1_CBC_CPT_LOINC_SNOM_INV_R |
| 12 | Investigation Report | CD Variable AA_Urinalysis_CPT_LOINC_SNO_INV |
| 13 | " | |

FROM FIG. 12A

FROM FIG. 12B

EG_2015 (i)
Effective Time < 6 mon    X
_NCCN_2014 (i)
Effective Time < 6 mon    ...

Count
Non Concurrent
Location
Device
Result Type
Time As
First Time As
Last Time As
Time is
During
Starts During
Ends During
Starts Before Start
Starts After Start
Starts After End
Starts Before End
Ends Before Start
Ends After Start
Ends After Ends
Location As
Location Is
✓ Capture Match Fact

FROM FIG. 12C

| Metric | Current Month Target | Current MTD Performance | Previous Month Delta | 2019 Target | Current YTD Performance | Previous Year Delta |
|---|---|---|---|---|---|---|
| Care Opportunities | | | | | | |
| Chronic Care Management | $12,384.00 | $14,512.50 | N/A | $1,390,065.30 | $14,512.50 | N/A |
| Advanced Care Plan | $4,800.00 | $4,000.00 | 3% | $16,000.00 | $15,200.00 | 2% |
| Annual Wellness Visit - Subsequent Visits | $6,553.80 | $7,149.60 | 21% | $17,874.00 | $19,065.60 | 15% |
| CVD Risk Reduction Visit | $1,576.80 | $1,839.60 | 4% | $5,256.00 | $4,993.20 | 3% |
| Unhealthy Alcohol Use Screening | $2,628.00 | $2,365.20 | 7% | $6,570.00 | $6,307.20 | 9% |
| Diabetes Screening | $436.50 | $465.00 | 3% | $1,091.25 | $1,139.75 | -2% |
| Bone Mass Measurement | $1,713.60 | $1,927.80 | 4% | $2,142.00 | $2,356.20 | -6% |
| Diabetes 6 Months F/U | $8,000.00 | $8,640.00 | 9% | $14,400.00 | $15,200.00 | 10% |
| DM Lab | $1,678.80 | $1,534.72 | 11% | $1,918.40 | $2,158.20 | 5% |
| HTN 6 Months F/U | $7,200.00 | $6,480.00 | 10% | $14,400.00 | $16,000.00 | 14% |
| Colorectal Screening | $1,045.00 | $950.00 | 5% | $1,520.00 | $1,425.00 | 6% |
| Breast Cancer Screening | $1,530.00 | $1,377.00 | -12% | $3,672.00 | $3,519.00 | -10% |
| Preventive Influenza Vaccine | $760.00 | $570.00 | 3% | $5,320.00 | $4,940.00 | 5% |

FIG. 14

HEALTH DATA PROCESSING AND SYSTEM

RELATED APPLICATIONS

This application claims the benefit under 35 U.S.C. § 119(e) of U.S. Provisional Patent Application Ser. No. 62/987,749, filed Mar. 10, 2020, and titled "HEALTH DATA PROCESSING AND SYSTEM", which is hereby incorporated herein by reference in its entirety.

BACKGROUND

Appointment schedules and electronic health records (EHR) and may provide information to healthcare professionals such as physicians.

SUMMARY

According to one aspect of the disclosure, there is provided a method. The method comprises receiving healthcare data associated with one or more patients of a healthcare professional, inputting, to a statistical model, the healthcare data, and generating a workflow of the healthcare professional using an output of the statistical model. The workflow of the healthcare professional comprises an ordered list of a plurality of healthcare events for the healthcare professional.

In some embodiments, the plurality of healthcare events comprises at least one of a task, an alert, or an appointment request for the healthcare professional.

In some embodiments, the statistical model is configured to provide the output based on at least one of time, criticality, or clinical evidence associated with the healthcare data.

In some embodiments, the method further comprises prompting the healthcare professional to follow up with a first patient of the one or more patients.

In some embodiments, the prompting is performed based on a location of the healthcare professional.

In some embodiments, the method further comprises providing, in the workflow, in a first healthcare event of the plurality of healthcare events, an indication of a first patient of the one or more patients, and in response to a selection of the indication of the first patient, providing, to the healthcare professional, a profile of the first patient.

In some embodiments, the healthcare data comprises financial data.

In some embodiments, the statistical model comprises at least one of a rule-based model or a trained statistical model.

According to one aspect of the disclosure, there is provided at least one non-transitory computer-readable storage medium having instructions encoded thereon that, when executed by at least one computer processor, cause the at least one computer processor to perform a method. The method comprises receiving healthcare data associated with one or more patients of a healthcare professional, inputting, to a statistical model, the healthcare data, and generating a workflow of the healthcare professional using an output of the statistical model. The workflow of the healthcare professional comprises an ordered list of a plurality of healthcare events for the healthcare professional.

In some embodiments, the plurality of healthcare events comprises at least one of a task, an alert, or an appointment request for the healthcare professional.

In some embodiments, the statistical model is configured to provide the output based on at least one of time, criticality, or clinical evidence associated with the healthcare data.

In some embodiments, the method further comprises prompting the healthcare professional to follow up with a first patient of the one or more patients.

In some embodiments, the method further comprises providing, in the workflow, in a first healthcare event of the plurality of healthcare events, an indication of a first patient of the one or more patients, and in response to a selection of the indication of the first patient, providing, to the healthcare professional, a profile of the first patient.

In some embodiments, the healthcare data comprises financial data.

In some embodiments, the statistical model comprises at least one of a rule-based model or a trained statistical model.

According to one aspect of the disclosure, there is provided at least one non-transitory computer-readable storage medium having instructions encoded thereon that, when executed by at least one computer processor, cause the at least one computer processor to perform a method. The method comprises generating a graphical user interface (GUI) representing a workflow of a healthcare professional and providing the GUI representing the workflow of the healthcare professional to a display. The GUI representing the workflow of the healthcare professional comprises an ordered list of a plurality of GUI elements representing a respective plurality of healthcare events for the healthcare professional.

In some embodiments, the method further comprises inputting, to a statistical model, healthcare data of one or more patients of the healthcare professional and ordering the list of the plurality of GUI elements representing the respective plurality of healthcare events using an output of the statistical model.

In some embodiments, ordering the list of the plurality of GUI elements representing the respective plurality of healthcare events using the output of the statistical model comprises formatting a first GUI element representing a first healthcare event of the plurality of GUI elements representing the plurality of healthcare events to include one or more visual indicators of priority, urgency, or severity.

In some embodiments, the ordered list of the plurality of GUI elements comprises at least one of a GUI element representing a task, a GUI element representing an alert, or a GUI element representing an appointment request for the healthcare professional.

In some embodiments, the GUI representing the workflow of the healthcare professional comprises a GUI element prompting the healthcare professional to follow up with a first patient.

In some embodiments, the GUI representing the workflow of the healthcare professional comprises, in a first GUI element of the plurality of GUI elements, an indication of a first patient, that when selected, provides, to the healthcare professional, a GUI element representing a profile of the first patient.

BRIEF DESCRIPTION OF DRAWINGS

Various aspects and embodiments will be described with reference to the following figures. The figures are not necessarily drawn to scale.

Figure 3A:
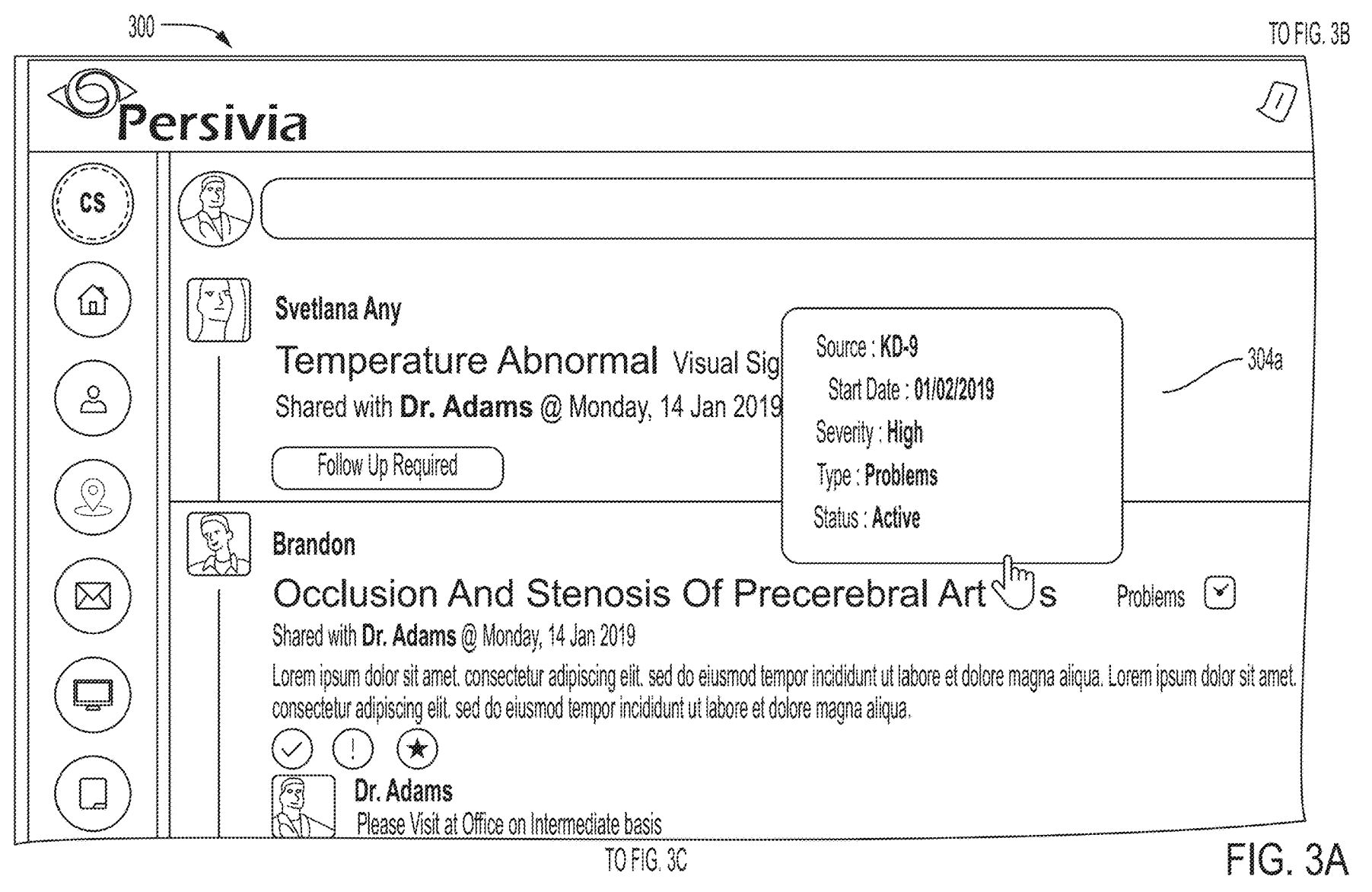

FIGS. 3A-3D show shows one embodiment of a GUI displaying a workflow of a healthcare professional;

FIGS. 4A-4D show one embodiment of a GUI displaying patient information;

FIGS. 5A-5D show one embodiment of a GUI displaying a follow up prompt for a healthcare professional;

Figure 6C:
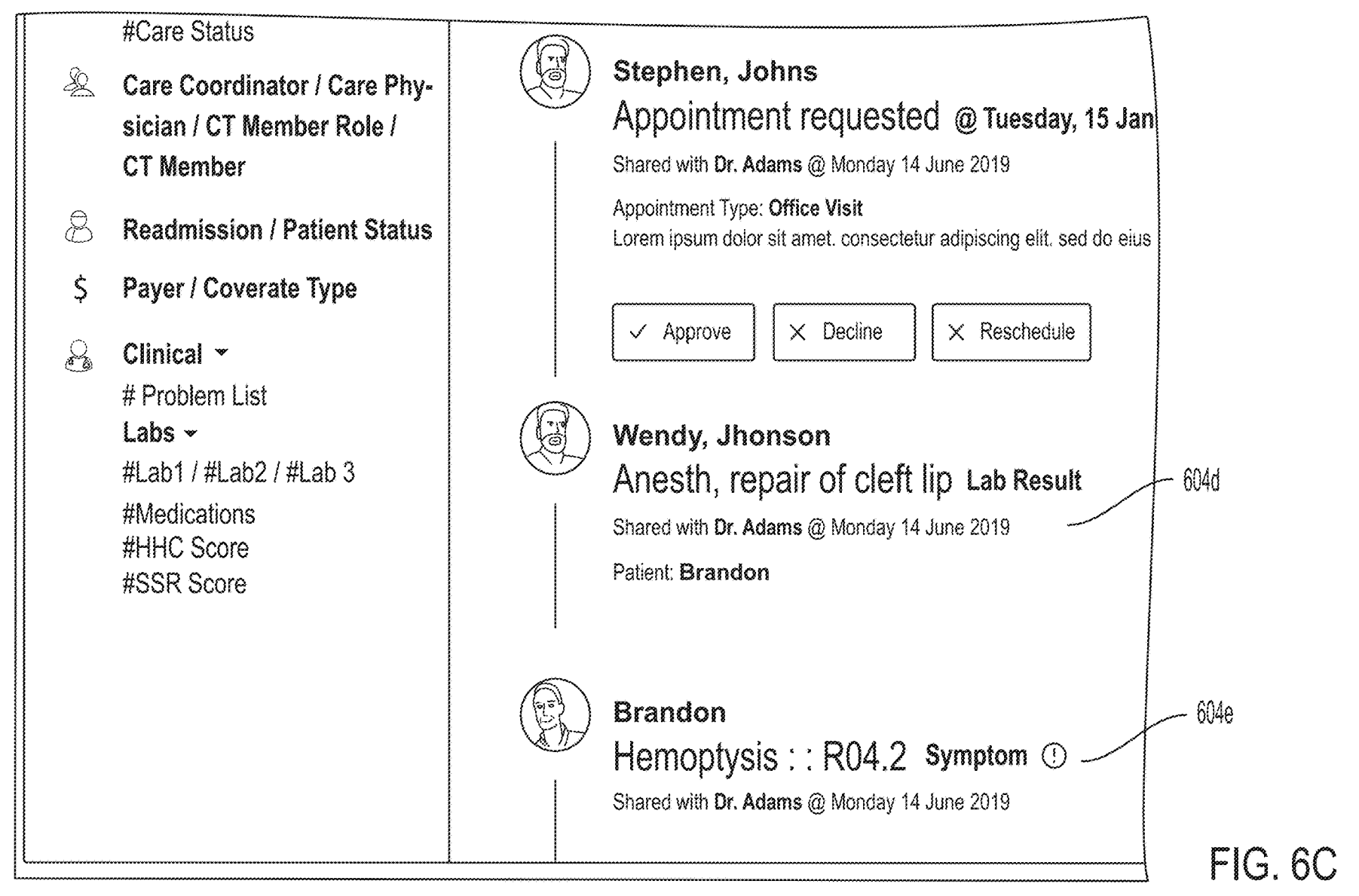

FIGS. 6A-6D show one embodiment of a GUI displaying a workflow of a healthcare professional;

FIGS. 9A-9D show one embodiment of a GUI for providing rules of a statistical model;

FIG. 11 shows one embodiment of displaying cost trends;

FIGS. 12A-12D show one embodiment of a GUI for providing rules of a statistical model;

FIG. 14 shows one embodiment of displaying care opportunity trends; and

DETAILED DESCRIPTION

Figure 1:
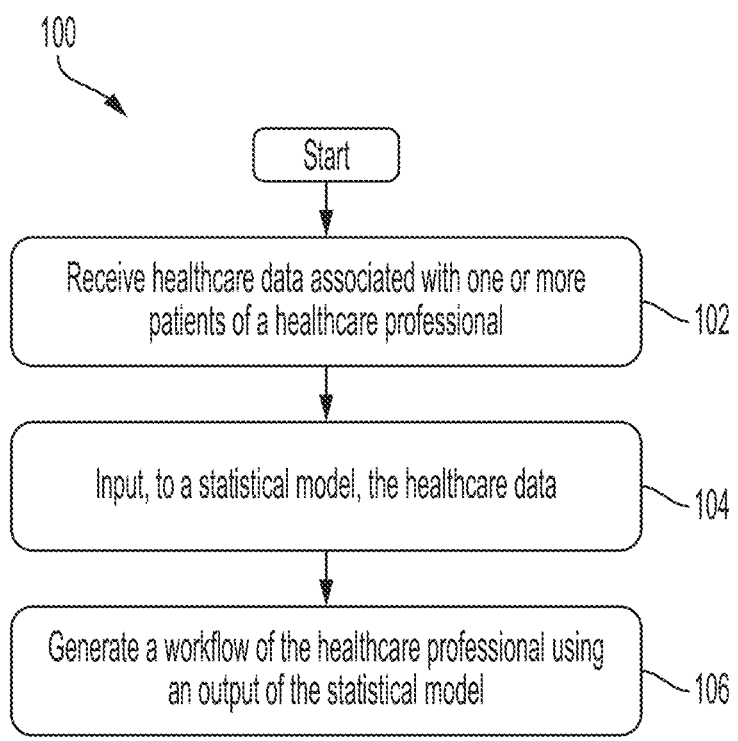
FIG. 1 shows a process flow of one embodiment of a method related to providing a workflow of a healthcare professional.

According to aspects of the present disclosure, there are provided methods for generating a workflow of a healthcare professional and methods of generating graphical user interfaces (GUI) that display the workflow of the healthcare professional. In some embodiments, a workflow of a healthcare professional may comprise an ordered list of healthcare events associated with the healthcare professional.

The inventors have recognized that conventional methods of managing the work of a healthcare professional may be inadequate. Generally, according to conventional methods, a healthcare professional may rely on an appointment schedule to determine what work needs to be completed. However, a conventional appointment schedule is merely a list including date and time of primarily in-person appointments with patients. The healthcare professional must view the appointment schedule and then refer to other information sources to complete any work that needs to be done. For example, the healthcare professional may refer separately to information in various electronic health records (EHR).

The inventors have recognized that it would be beneficial to provide a workflow for a healthcare professional. A workflow of a healthcare professional may include an ordered list of healthcare events associated with the healthcare professional. Each of the healthcare events in the ordered list may request the attention of the healthcare professional or may provide an indication that the healthcare professional should complete some associated work. For example, each healthcare event in the order list may be a task for the healthcare professional to complete, an alert such as new lab results for a patient of the healthcare professional that the healthcare professional should be aware of, a scheduled appointment with a patient of the healthcare professional, or an appointment request from a patient of the healthcare professional. In some embodiments, the workflow may provide a healthcare professional with, in one user interface, all, substantially all, or a majority of the healthcare events that the healthcare professional should to be aware to perform their job.

Workflows and associated GUIs described herein may provide various benefits. A workflow may allow a healthcare professional to perform their job more efficiently and effectively, with respect to both patient care and financial objectives. For example, such a workflow may function as a single hub that the healthcare professional must monitor to be aware of all, substantially all, or a majority of healthcare events associated with their job. Instead of referring to various different appointment schedules and electronic health records (EHR), the healthcare professional may focus their attention on one resource. Additionally, workflow of the types described herein may assist a healthcare professional with planning of non-scheduled work. Instead of requiring a healthcare professional to plan work themselves based on upcoming appointments, as with a conventional appointment schedule, a workflow of the types described herein may provide a healthcare professional with healthcare events in an ordered list. The healthcare professional may review the healthcare events and perform any associated work in the order that the events appear in the list. Additionally, the list may be ordered in a manner provide more effective care to patients. For example, the list may be ordered based on criticality or clinical evidence associated with each healthcare event, which may ensure that patient care is administered in the most effective order. Similarly, the ordering of the list may be based on financial programs to provide financial benefits.

A list of healthcare events making up a workflow of a healthcare professional may be ordered based on the output of a statistical model. In various embodiments, a statistical model may include at least one of a rule-based model or a trained statistical model, for example, a trained statistical model generated via machine learning algorithms. Such a statistical model may be programmed to receive healthcare data as input and provide, as output, information for generating the workflow of the healthcare professional. The statistical model may be programmed to provide its output based on time, criticality, or clinical evidence associated with the healthcare events to be included in the ordered list. For example, more recent events, more critical events, or events with stronger clinical evidence may be given higher ordering in a list of events.

In some embodiments, a workflow may include an indication of a patient that may be selected by a healthcare professional to access a page of information for that patient. In some embodiments, a workflow of a healthcare professional may include a prompt to the healthcare professional to follow up patient. For example, the prompt may be generated based on a location of the healthcare professional and a location of the patient. If it is determined that the healthcare professional will have a similar location to a patient, the workflow may prompt the healthcare professional to schedule an appointment while in the area of the patient.

Statistical models described herein may be trained according to any suitable method. For example, healthcare data may be obtained to use as input to a statistical model. Training data may be acquired for the statistical model. A machine learning module may then train the statistical model using the healthcare data and the training data. The machine learning module may output a trained statistical model programmed to receive healthcare data as input and provide, as output, information for generating a workflow of a healthcare professional. The trained statistical model may also be stored in an appropriate non-transitory computer readable storage medium for subsequent use.

Aspects of the disclosure relate to an artificial intelligence-based system for managing the healthcare of a person in a complex community. According to some embodiments, systems described herein may be powerful and user-friendly and assist with care and communication between patients, healthcare providers, payers, and payees. Systems may include a user interface, artificial intelligence layers including an artificial intelligence engine, and a data warehouse. Each of the user interface, artificial intelligence layers and underlying artificial intelligence engine, and data warehouse components is described in further detail herein.

Aspects of the disclosure provide various user interfaces. The user interfaces described herein may comprise graphical user interfaces (GUIs). A system may comprise a unified user interface configured to be used by all healthcare stakeholders.

In some embodiments, user interfaces may provide particular layouts of information. For example, the user interface may use an artificial intelligence engine described herein to determine the layout of the information displayed. Information layout may be different for different workflows. In some embodiments, presented information may also be available to other users. For example, for users having access to a system, the actions of each user, including changes and updates, may immediately be made available to other users. In some embodiments, changes and updates may be made available if an artificial intelligence engine determines that the other user or the patient would benefit from having access to the new information.

In some embodiments, the user interface may provide artificial intelligence-driven workflows that determine the order in which information is presented in the user interface. For example, the user interface may use the artificial intelligence engine to provide an ordered list of healthcare events.

In some embodiments, the user interface may use an artificial intelligence to determine information and data that will be used to determine a next steps that are to be taken by users such as healthcare professionals.

In some embodiments, the user interface uses an artificial intelligence engine to present options to users such as healthcare professionals for next steps. Information presented to a user for next steps may include information to provide to each user, actions that are to be performed by each user in real time, appropriate information, forms and actions requested by users on demand, or other information.

A system may provide a particular layout of information in a provider view for a healthcare professional. For example, a system may provide a workflow for the healthcare professional.

Figure 2:
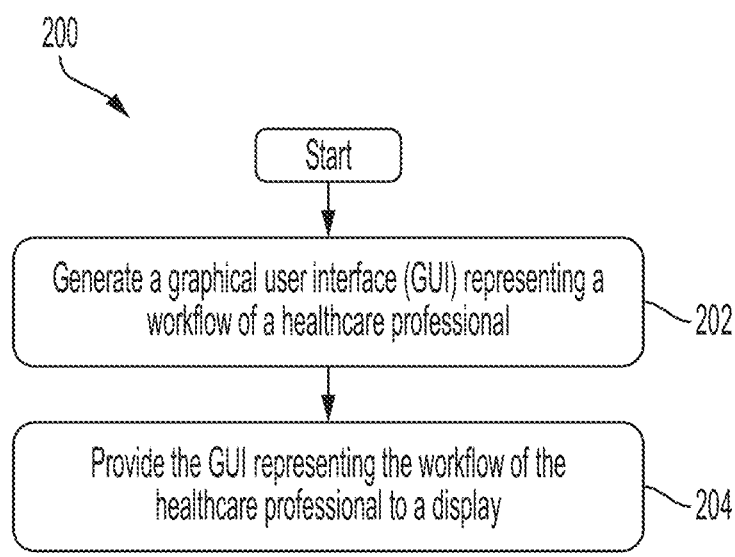
FIG. 2 shows a process flow of one embodiment of a method related to providing a graphical user interface (GUI) for a healthcare professional.
Figure 3B:
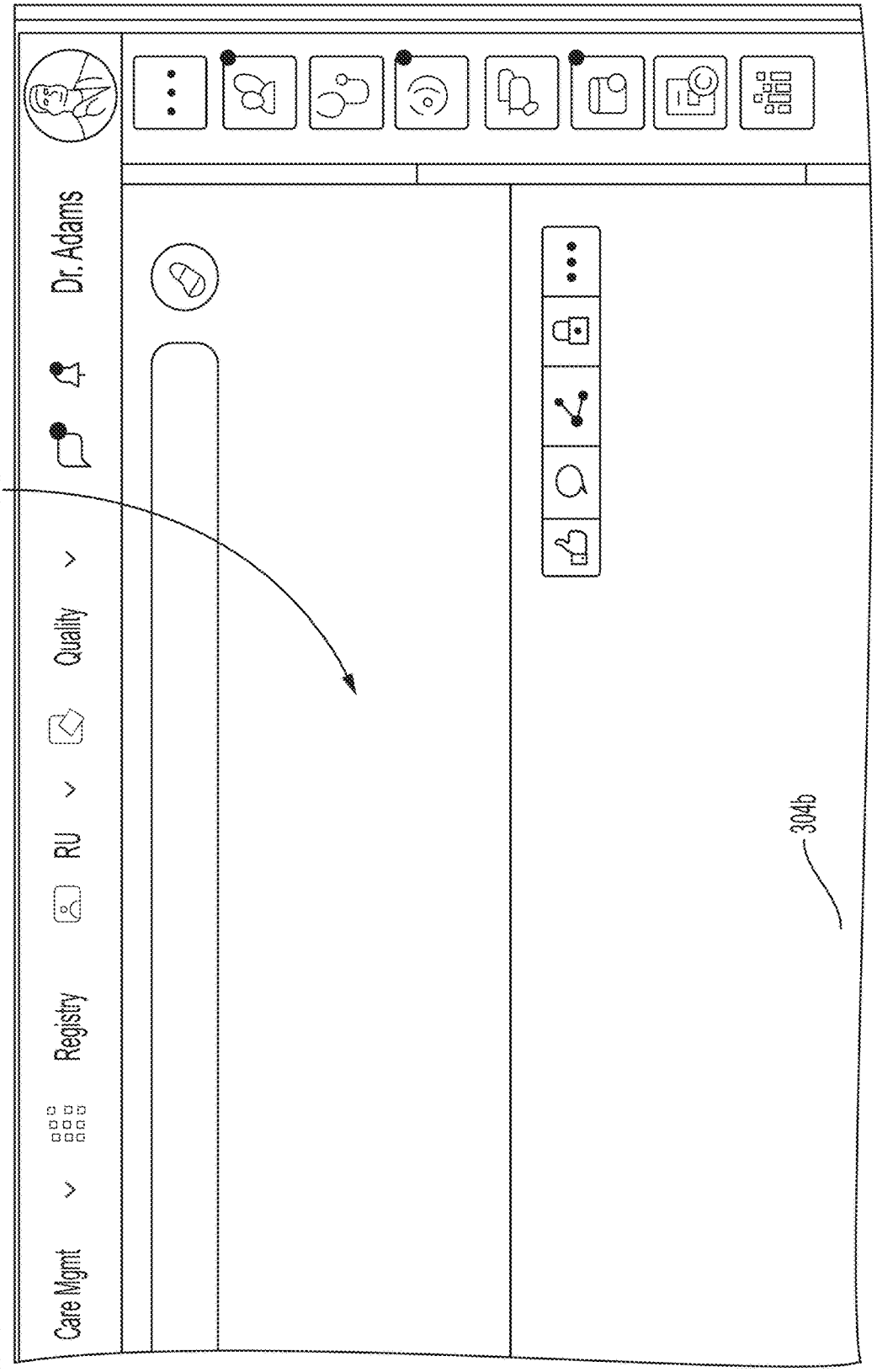
Figure 4B:
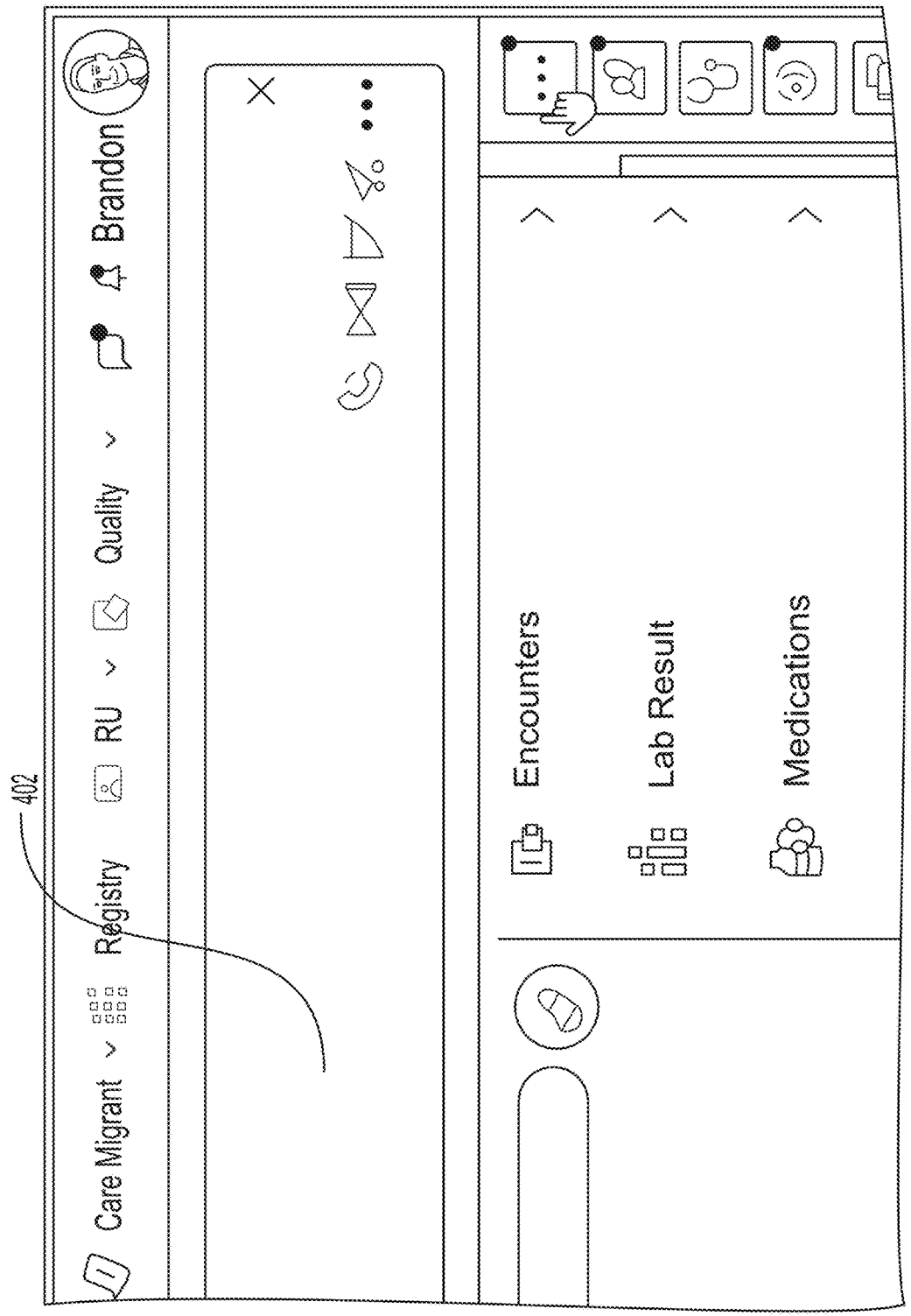
Figure 4C:
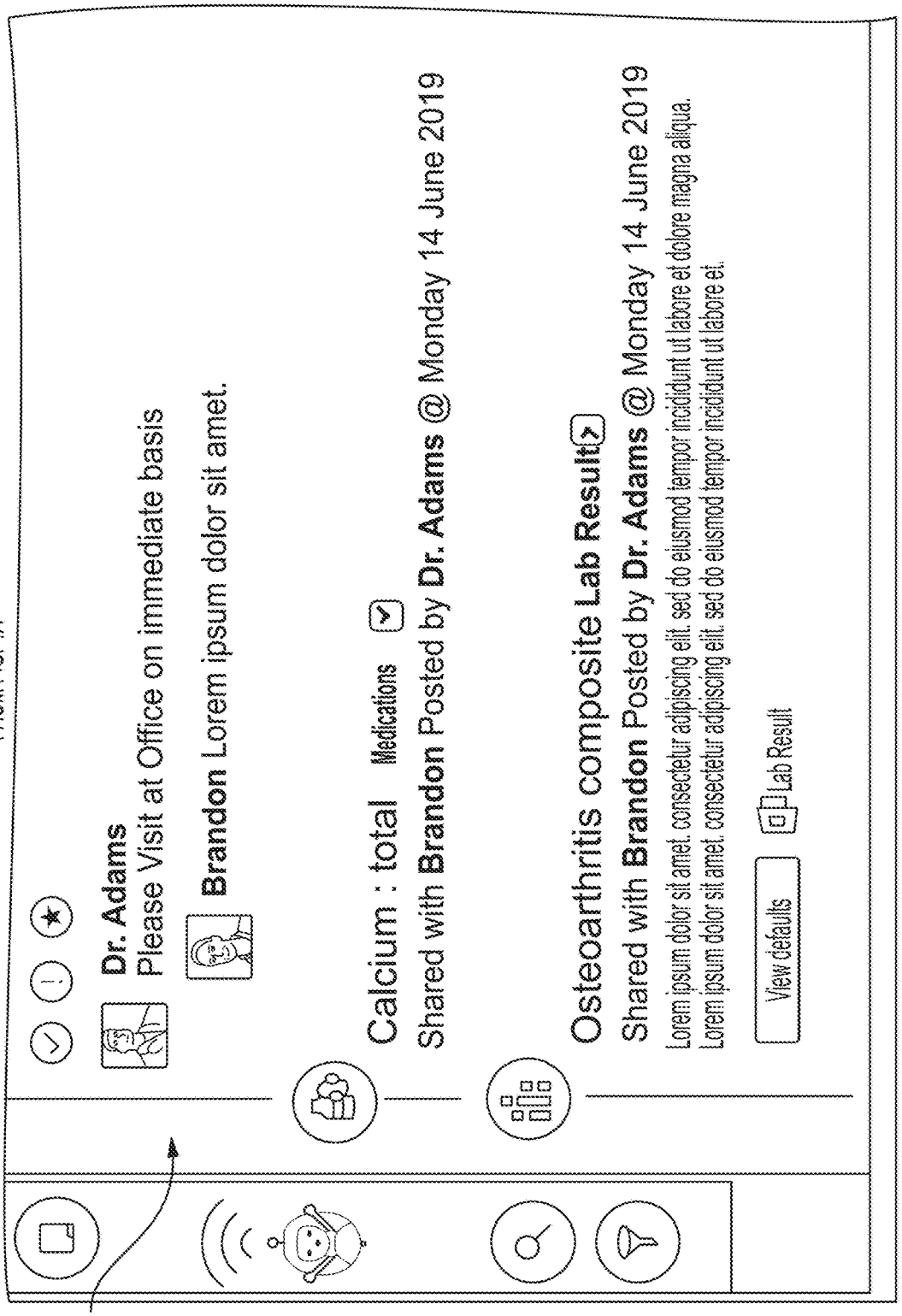
Figure 4D:
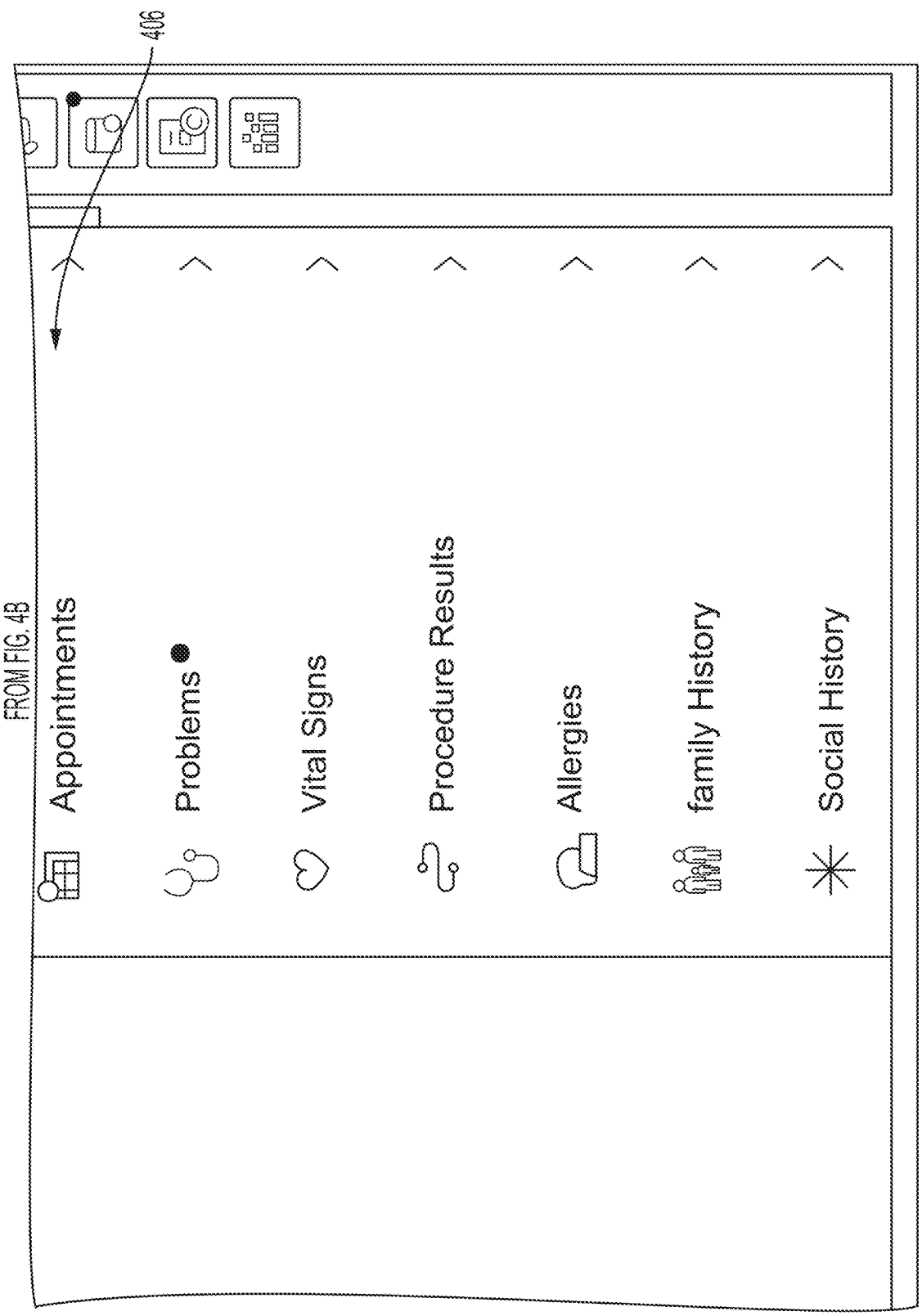
Figure 5A:
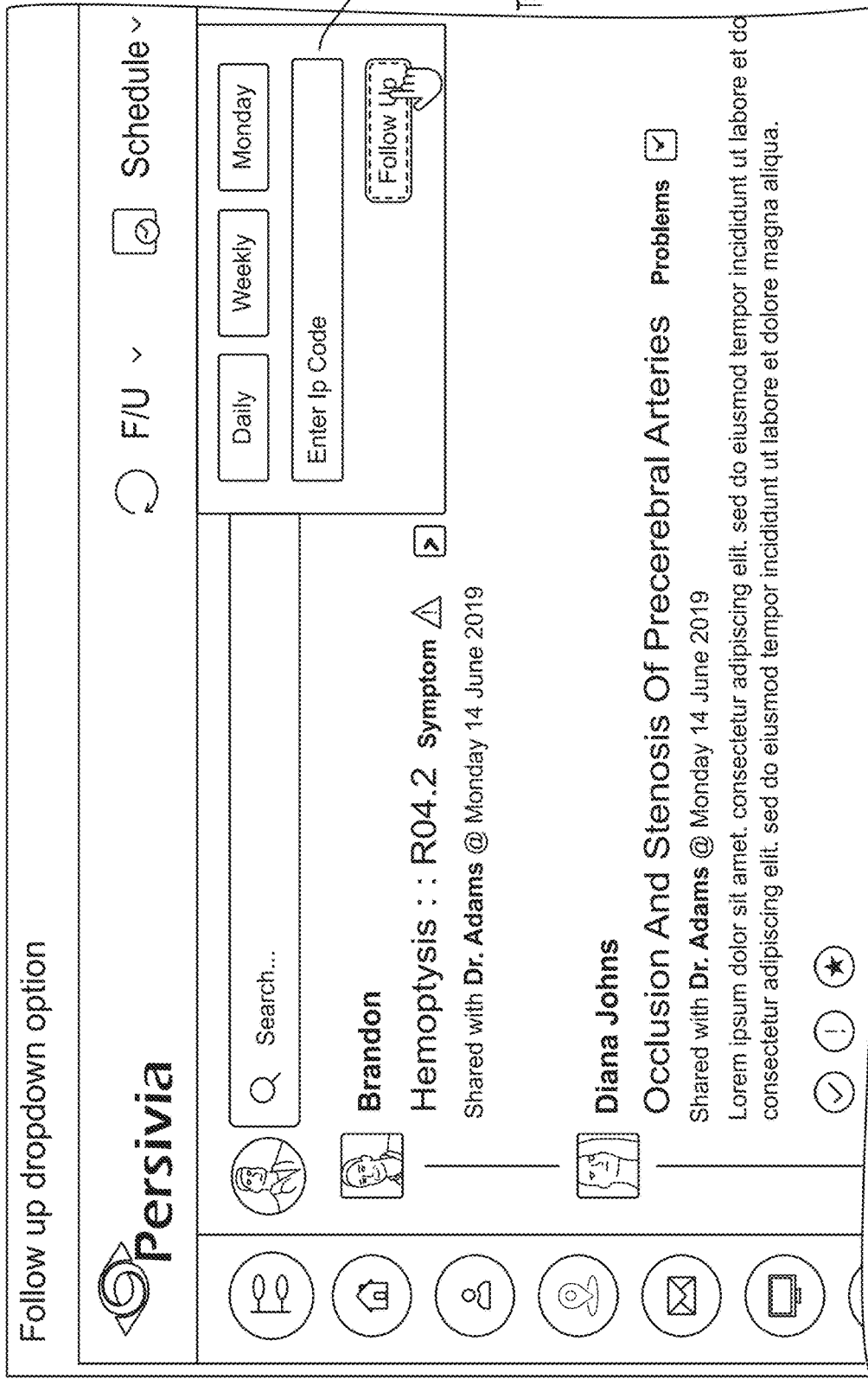
Figure 5B:
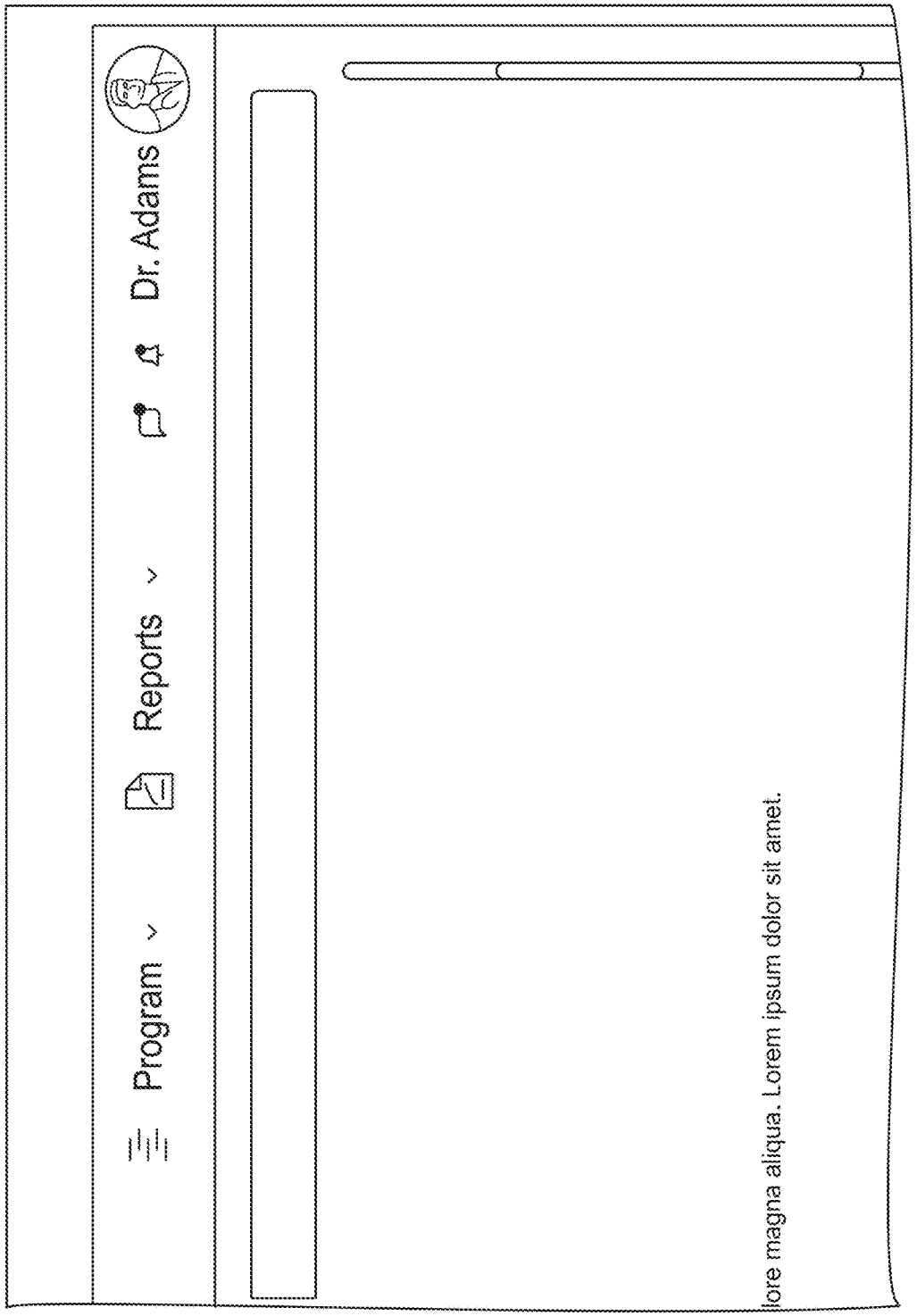
Figure 5C:
Figure 6A:
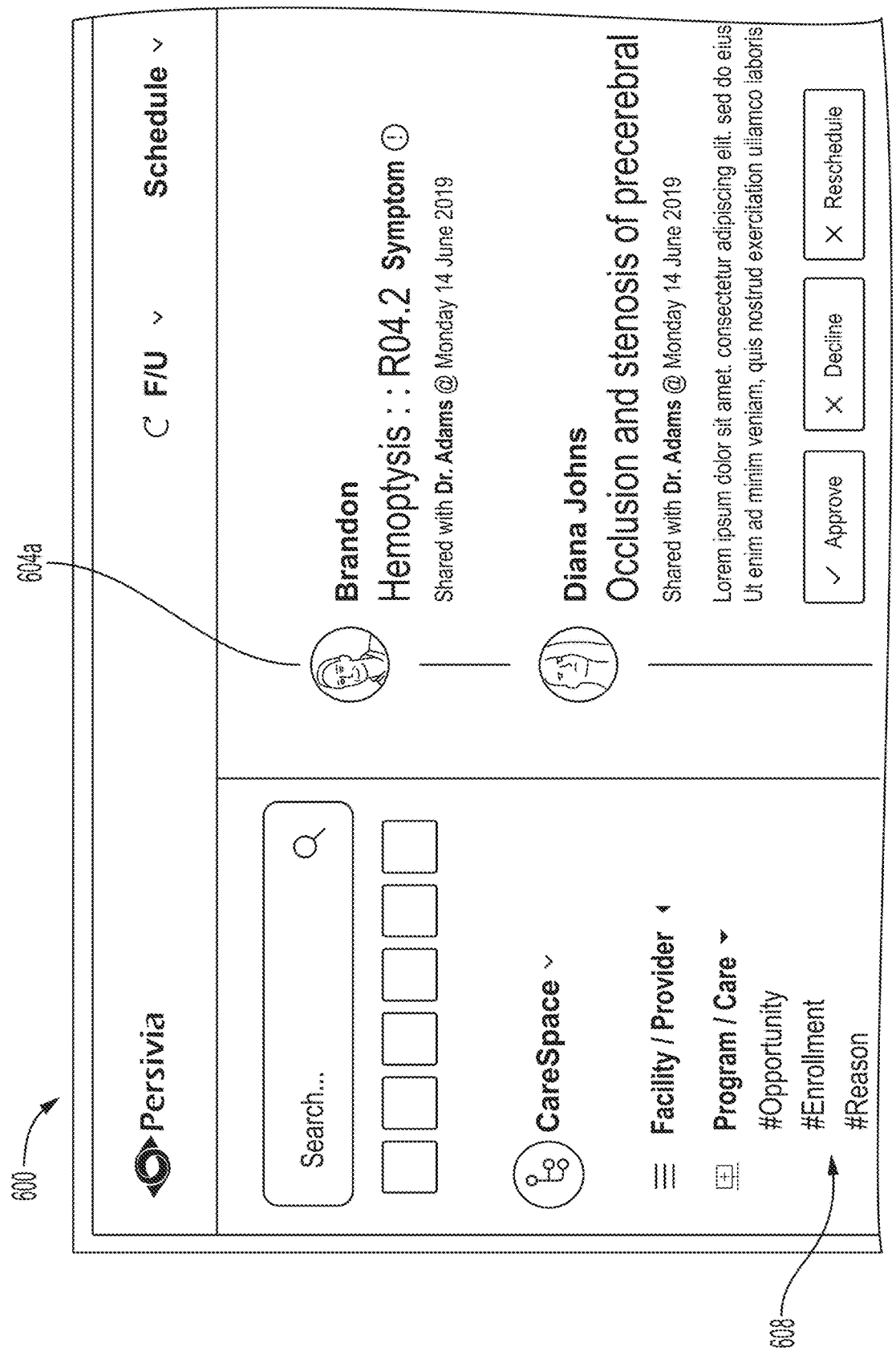
Figure 6B:
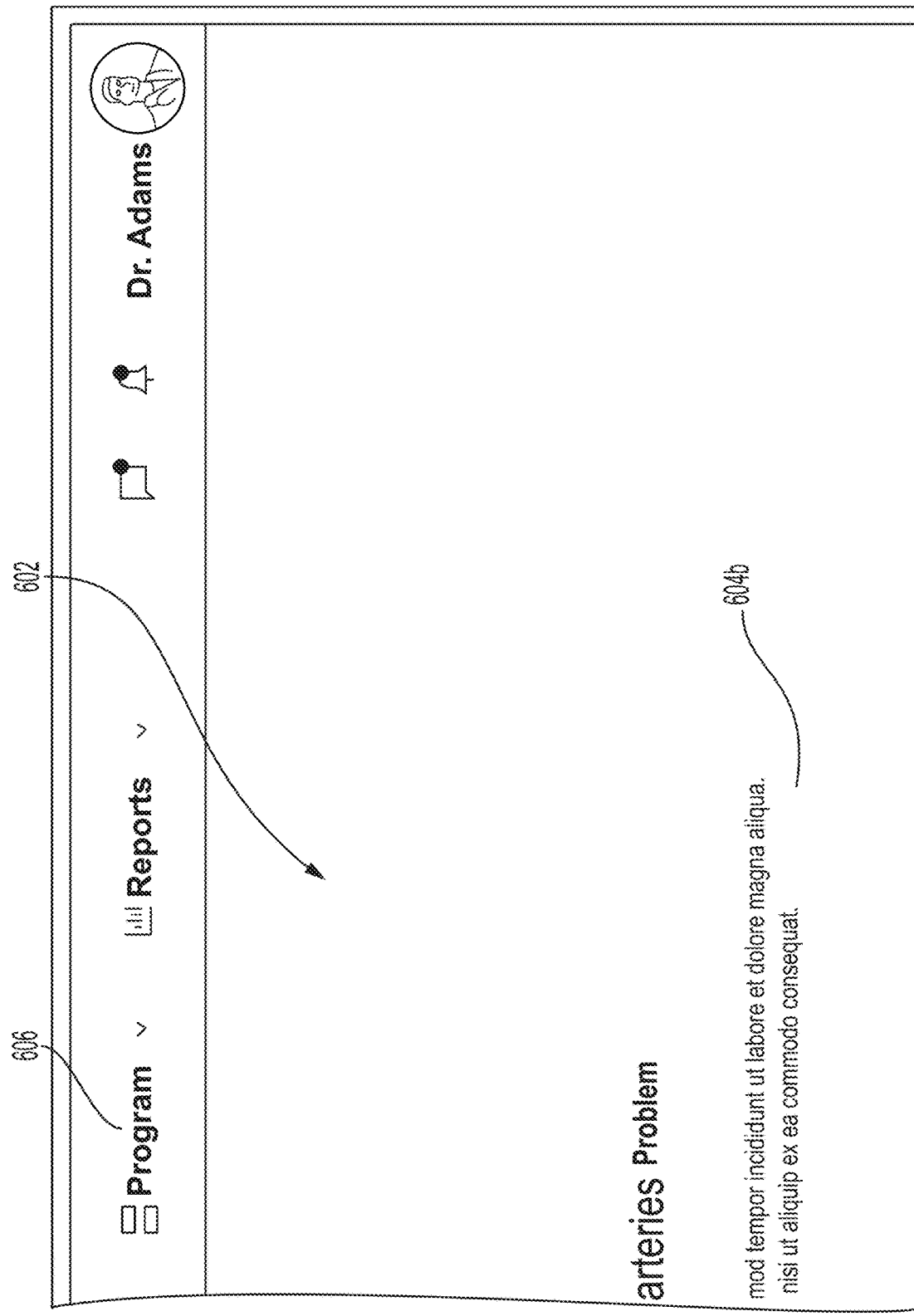
Figure 6D:
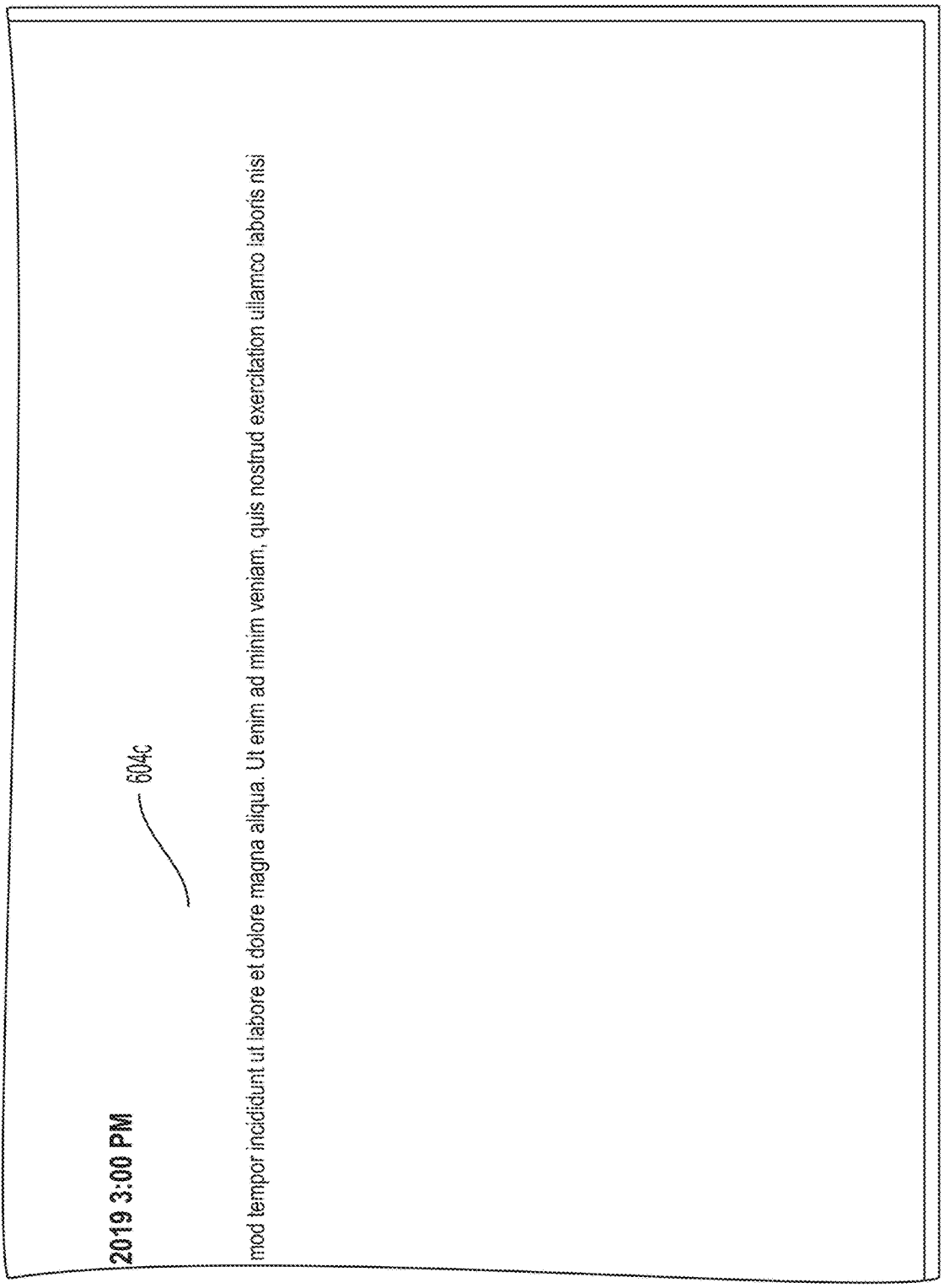

FIG. 1 shows a process flow 100 of one embodiment of a method related to providing a workflow of a healthcare professional. The process flow 100 may be performed by at least one computer processor. In some embodiments, there may be at least one non-transitory computer-readable storage medium encoded with a plurality of instructions that, when executed by at least one computer processor, perform process flow 100. Process flow 100 comprises step 102, step 104, and step 106. In step 102, the at least one computer processor receives healthcare data associated with one or more patients of a healthcare professional. In step 104, the at least one computer processor inputs, to a statistical model, the healthcare data. In step 106, the at least one computer processor generates a workflow of the healthcare professional using an output of the statistical model. In some embodiments, the workflow of the healthcare professional comprises an ordered list of a plurality of healthcare events for the healthcare professional FIG. 2 shows a process flow 200 of one embodiment of a method related to providing a GUI for a healthcare professional. The process flow 200 may be performed by at least one computer processor. In some embodiments, there may be at least one non-transitory computer-readable storage medium encoded with a plurality of instructions that, when executed by at least one computer processor, perform process flow 200. Process flow 200 comprises step 202 and step 204. In step 202, the at least one computer processor generates a GUI representing a workflow of a healthcare professional. In step 204, the at least one computer processor provides the GUI representing the workflow of the healthcare professional to a display. In some embodiments, the GUI representing the workflow of the healthcare professional comprises an ordered list of a plurality of GUI elements representing a respective plurality of healthcare events for the healthcare professional. In various embodiments, a display may comprise a visual display, an audio display, a tactile display or another display, A visual display may comprise a computer screen or other screen.

In some embodiments, a GUI element may provide links to each of several different workflows, icons linking to message and alert sections, information indicating an identity of the healthcare professional, for example, a name and a picture. This GUI element may be located at a top of the GUI.

The GUI may include an alert icon link. In some embodiments, a selection of an alert icon may open window, which may be an overlay window, that displays a list of patients, providers, or other care takers, a healthcare event related to that user or sender, and one or more plan of treatment actions for responding to the healthcare event.

A user interface may provide various workflows, such as a timeline, a work list, or an analytics or population view. Layout of the GUI may change depending on which of these various workflows is selected by a user.

In some embodiments, a user interface may order a list of healthcare events spatially in the user interface. For example, a healthcare event having a higher ordering may be displayed spatially higher in the list than other healthcare events, in the user interface, or way be spatially ordered in another manner.

For example, FIGS. 3A-3D show one exemplary embodiment of a GUI 300 a workflow of a healthcare professional. GUI 300 includes a GUI element 302 representing a workflow of the healthcare professional. In the illustrative embodiment, the GUI element 302 representing the workflow comprises an ordered list of healthcare events 304*a*, 304*b*, 304*c*, and 304*d* for the healthcare professional. The healthcare events may include any of the healthcare events described herein, including, but not limited to, any of a task, an alert, for example, a lab results alert, a scheduled appointment, or an appointment request for the healthcare professional. The healthcare events 304*a*, 304*b*, 304*c*, and 304*d* may be ordered in the GUI element 302 according to various factors. In some embodiments, healthcare events may be ordered based on a combination of time, criticality, and clinical evidence. For example, a healthcare event associated with a more recent time may be given a higher ordering in a list than a healthcare event associated with a less recent time. In some embodiments, a healthcare event deemed more critical may be given a higher ordering in a list that a healthcare event deemed less critical. A healthcare event associated with stronger clinical evidence may be given a higher ordering in a list than a healthcare event associated with weaker clinical evidence. In some embodiments, the ordering of the list may be determined using the output of a statistical model of one of the types described herein. The input to the statistical model may include any of the healthcare data described herein.

In a timeline workflow, healthcare events may be displayed in the GUI an order in which they occur along a timeline. For each healthcare event, the GUI may further display a sequence of healthcare events preceding the healthcare event. In some embodiments, the preceding healthcare events may be provided in a collapsed view in the GUI and may be collapsed by a user individually or all at once.

A timeline workflow may show for each healthcare event, at a first level, components including, but not limited to, any of an indication of a patient, such as a name and picture, if available, of the patient, a description of the healthcare event, which may be provided in a largest font and represent a headline of the healthcare event, a type of healthcare event, for example, diagnosis, lab, vital sign, which may be provided in a medium font, with a button to open a window showing the source, date, severity, type, and status of the healthcare event, a date and time when the healthcare event showed up in the system and which provider was the source of the healthcare event, for example, if the source was a different healthcare provider, details of the event, which may be provided in a smallest font, a plan of treatment section of the healthcare event, or a specific workflow icons.

In some embodiments, a plan of treatment action section may be displayed as a set of buttons or icons with or without text labels, and may include, but are not limited to, any of approve, decline, accept or accepted, follow up, schedule or reschedule, admit, discharge, prescribe, order, transfer, refer. In some embodiments, the specific workflow icons may appear when they are due, or may be always visible if they are doable at any time, and may include, but are not limited to annual wellness visits, face to face visits, or tele-visits.

In some embodiments, a GUI may allow a user to select a healthcare event. Selection of a healthcare event may trigger display of a new page for a patient to whom the healthcare event is related. FIGS. 4A-4D show an exemplary patient page GUI 400. In the GUI, a patient page may include a GUI element comprising a panel across a top of the GUI that displays the demographic information of the patient. For example, GUI element 402 may comprise a demographic patient panel. In some embodiments, a demographic patient panel may display information such as which programs a patient belongs to, as well as information representing risk scores and costs of care of the patient along with a benchmark for the program, which may be displayed as a chart. The GUI may further display a date of last visit, next visit, procedures, or medications due, any hospital or ER admissions or readmissions, or quality or care gaps for a current period.

A patient page GUI may include its own timeline displaying all the events related to that patient in the order they occurred. For example, FIGS. 4A-4D show patient timeline 404. A patient page GUI may also include a set of icons or links that display a menu list of all datums that are supported by the artificial intelligence engine, for example, encounters, labs, diagnoses, medications, appointments, allergies. FIGS. 4A-4D show a datum list 406.

In some embodiments, a patient page may be accessed in the GUI by searching a list of all patients. In some embodiments, a patient list may include an icon next to each patient displaying a list of actions that the healthcare professional may take with respect to that patient the provider can take regarding that patient without requiring that the specific patient page be opened.

Aspects of the disclosure provide methods for formatting healthcare data. A user interface may display information based on algorithms that manage various datums. For example, the datums may include problems, labs, risk factors, risk scores, medications, device data, patient generated data with various weights or scores, generated in various ways included being determined by an eigen value, based on a machine learning algorithm, assigned to them. An artificial intelligence layer may calculate a weight assigned to every datum. In some embodiments, datums may have a positive or a negative weight. For example, healthy BMI, PHQ 9 negative screen, steady employment status, college or graduate education may have a negative score. On the other hand, attributes such as chronic and acute conditions, high risk or long-term medications, ER and hospital visits will have a positive score. In some embodiments, in addition to a score, each attribute may have a priority independent from the weighting. For example, a high lab result may have low or high priority depending on what is the immediate impact on the health of that particular patient in the context of their health. As an example, a low hemoglobin value may result in different priority in a healthy patient than for a patient with a red blood cell disorder. Similarly, the priority of a particular datum may also change in depending on the overall well-being of the patient.

In some embodiments, a user interface may order a list of healthcare events using formatting. For example, a healthcare event having a higher ordering may be displayed with one or more visual indicators. In some embodiments, the visual indicators may indicate priority, urgency, severity, or another aspect of a healthcare event. In some embodiments, ordering of lists using formatting may be performed instead of or in addition to spatial ordering of a list.

In a user interface, one or more visual indicators may be used to indicate priority, urgency, or severity of information. Priority of information may fall along a scale from highest to lowest priority. The one or more visual indicators of priority may include font bolding, for example, to show priority or urgency, color coding, for example, to show severity, or other formatting to communicate urgency, priority, and severity. Information having a highest weight may be displayed with a largest font.

In some embodiments, formatting may be performed using a statistical model of one of the types described herein. For example, a healthcare event in a workflow may be formatted to include one or more visual indicators based on an output of a statistical model. In some embodiments, ordering a list of healthcare events using a statistical model may include formatting the GUI elements representing the healthcare events to include one or more visual indicators. For example, if the output of the statistical model indicates that a healthcare event has a particular priority, urgency, or severity, the user interface may include, in a GUI element for the healthcare event, a visual indicator representing that priority, urgency, or severity. The input to the statistical model may include any of the healthcare data described herein.

Aspects of the disclosure provide methods for displaying and using healthcare information. In some embodiments, displayed information may be governed by an artificial intelligence engine. A system may provide a workflow based on the output of the artificial intelligence that addresses the changing healthcare landscape of providing care in all settings. For example, healthcare may be provided through multimodal, synchronous and/or asynchronous capabilities. The user interfaces described herein are arranged to increase the productivity of a healthcare professional by providing a workflow based on information driven by the artificial intelligence, allowing the healthcare professional to quickly complete tasks.

In some embodiments, a workflow may include a prompt to follow up with a patient. For example, FIGS. 5A-5D show an exemplary patient follow up GUI 500. Patient follow up GUI 500 includes a follow up prompt 502. In some embodiments, a workflow may include a follow up list of patients that may be quickly and easily sorted by a user. For example, the follow up list may be sorted by time to follow up, for example, daily, weekly, monthly, annual, or another length of time. The follow up list may be sorted by location of the patient and/or the healthcare professional, for example, based on zip code. Sorting a follow up list based on patient and/or healthcare professional location information may allow the healthcare professional to plan visits or outreach when the healthcare professional is in a particular area. In some embodiments, a follow up list may be sorted based on patient status. For example, patients with a more critical health status may be sorted to a top of the list. Sorting a follow up list based on patient health status may enable a healthcare professional to provide outreach based on which patients may benefit the most from attention.

A user interface may include a display of scheduled appointments. For example, a tab in the GUI for scheduled patients may display patients who are already part of a schedule.

In addition, a user interface may include a display of programs. For example, a tab in the GUI may display to a user, different programs, for example those derived from evidence-based medicine (EBM). In some embodiments, programs may include ePrograms. Programs may inject the latest medical evidence at different points in a healthcare journey of a patient. For example, program eligibility may be driven by an artificial intelligence engine. The artificial engine may capture various datums to construct a wide cohort, for example, all patients with diabetes, or a narrow cohort, for example, all patients aged greater than 65 years, without any insurance, and with medication possession ratio of 0.3 for diabetes medications. In some embodiments, the user interface may display to a user, reports and graphs based on metrics such as attribution, programs, utilization, care, risk stratification, evidence based medicine (EBM) rules and trained statistical models such as machine learning-based models.

For example, FIGS. 6A-6D show one exemplary embodiment of a GUI 600 a workflow of a healthcare professional. GUI 600 includes a GUI element 602 representing a workflow of the healthcare professional. In the illustrative embodiment, the GUI element 602 representing the workflow comprises an ordered list of healthcare events 604a, 604b, 604c, 604d, and 602e for the healthcare professional. GUI 600 may differ from GUI 300 in that GUI 600 includes a GUI element 606 representing an icon link for accessing program information. Accordingly, GUI 600 provides, within the workflow of a healthcare professional, access to program information to the healthcare professional.

A GUI may also include a GUI element configured to filter a workflow comprising an ordered list of healthcare events. For example, GUI 600 comprises GUI element 608. GUI element 608 represents a filter. The user interface may provide filters using a statistical model. For example, the user interface may select a set of one or more filters based on an output of a statistical model. The input to the statistical model may include any of the healthcare data described herein. A filter may be selected by a healthcare professional to filter the workflow comprising the ordered list of healthcare events so that the healthcare professional may focus on particular healthcare events of interest to the healthcare professional. Within a filtered list of healthcare events, the healthcare events may also be ordered according to the ordering techniques described herein. In some embodiments, a GUI element may include filters such as facility or provider, program aspects or care aspects, (for example, aspects may include opportunity, enrollment, reason, care status), care coordinator, care physician, care team (CT) member role, or CT member, readmission or patient status, payer or coverage type, clinical (for example, a problem list, labs, medications, or risk scores).

Aspects of the disclosure provide various communication modalities in a user interface. User interfaces described herein may provide communication between users regarding a patient and their care, for example, one to one, one to many, or many to many communication.

The system may support communication modalities including, but not limited to, any of instant messaging, email, such as email integration with existing email applications including Outlook, Mail, Gmail, Yahoo mail, and others, real time video or stored and forwarded video, landline telephone integration, mobile integration, social media integration, Facebook, Google, WhatsApp, or other communication modalities.

Figure 7:
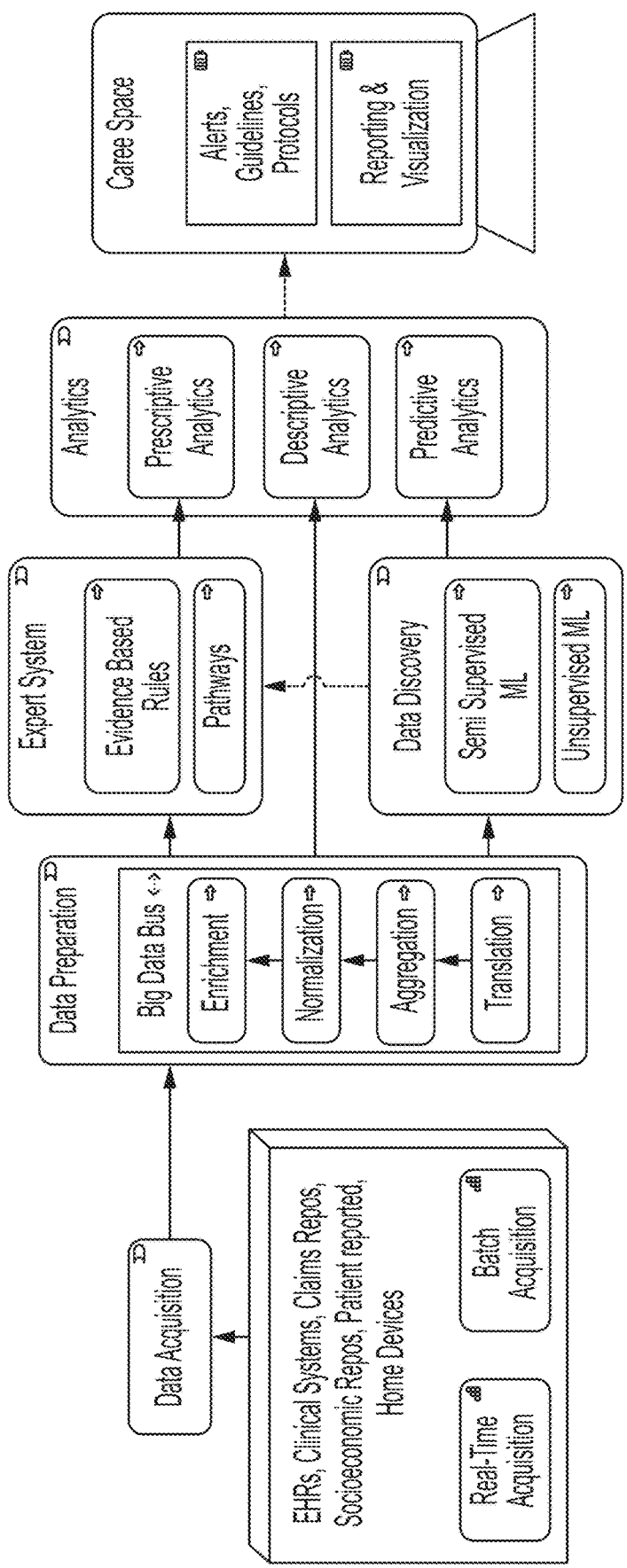
FIG. 7 shows a process flow of one embodiment of a method related to providing a workflow of a healthcare professional.

According to some embodiments, systems described herein employ functions including data preparation, data discovery, rules-based functions by an expert subsystem, and analytics. FIG. 7 shows one exemplary process flow of some methods described herein.

In some embodiments, data preparation may include translation, aggregation, normalization, and enrichment steps. In some embodiments, data may be processed in real time. To process data in real time, systems may utilize a fully distributed and scalable data preparation process comprising distributed processing nodes, distributed asynchronous communication channels, and high performance massively scalable persistence layers. In some embodiments, a distributed processing node may utilize a Microservices architecture to scale. In some embodiments, a distributed asynchronous communication channel. For example, a distributed asynchronous communication channel may comprise a high throughput, low latency, real time platform distributed processing tool, such as Kafka. A distributed asynchronous communication channel may provide temporary storage while a destination program is busy or not connected. In some embodiments, for data processing, a system may use a distributed, wide-column storage, such as Cassandra. In some embodiments, wide-column storage provides fast write functions by virtue of a storage engine using a log-structured merge tree. In some embodiments, wide-column storage may provide a distributed, horizontally scalable NoSQL DB. Wide-column storage may not have a single point of failure by using a masterless clustering mechanism.

In a translation step, multiple distributed transformer nodes may perform transformation of healthcare data by converting acquired healthcare data from a plurality of different supported formats into a single format. A translation step may include translation of unstructured healthcare data. For example, unstructured data may be tagged and passed to a natural language processing (NLP) processor. In an aggregation step, a system may identify entities associated with healthcare data and compile different entity feeds into a common consolidated entity. In a normalization step, a system may structure healthcare data according to a series of normal forms to reduce data redundancy and improve data integrity. In an enrichment step, a system may identify and add curated, high-quality differently-structured healthcare data to a single consistent data structure.

Aspects of the disclosure provide data discovery. In some embodiments, data discovery may be a capability of a system to gain from information without being given an explicit target. Data discovery may depend on the use of unsupervised or semi-supervised machine learning methods, for example, segmentation, dimensionality reduction, recommendation, and/or anomaly detection systems.

In complex datasets, it may be difficult to ask the right questions. To find value from data, it may be beneficial to have an understanding of the relationships that are inherent and important in the data, which may benefit from a principled approach to hypothesis generation.

The algorithms described herein surface hidden connections that exist in the healthcare data and recognize relationships that are meaningful without asking explicit questions of the data, allowing enterprises to find answers to questions they didn't even know to ask.

Systems described herein may be knowledge-based systems. In some embodiments, a knowledge base comprises thousands of facts fed into the system in the form of rules. In some embodiments, rules may work by querying and asserting values of entities that are fed large data sets passed through data preparation and machine learning phases.

In some embodiments, a system may include an inference engine. An inference engine may be an automated reasoning system configured to evaluate a current state of a knowledge base, apply relevant rules, and asserts new knowledge into the knowledge base.

After a data set is understood using intelligent discovery, supervised methods may be applied to predict what will happen in the future, including classification, regression, and ranking.

At a prediction step, systems may utilize a set of supervised machine learning algorithms including, but not limited to, any of random forests, gradient boosting, linear or sparse learners. Discovery capabilities of the systems described herein may be used to find relevant features such as pathways.

Systems according to aspects of the disclosure provides different types of analytics to fulfill relevant business needs, such as descriptive analytics, predictive analytics, or prescriptive analytics. In some embodiments, descriptive analytics may provide insights to past and current doings. Descriptive analytics may be provided to related business components in substantially real-time. Data preparation and related business processing steps described herein may serve as the input for descriptive analytics. In some embodiments, predictive analytics may forecast a prediction of what might happen in the future. The data discovery and machine learning components described herein use a variety of statistical, modeling, data mining, and machine learning techniques to study recent and historical data, to provide predictions about the future. In some embodiments, prescriptive analytics may prescribe one or more actions to the right audience at the right moment. Prescriptive analytics may utilize the machine learning algorithms described herein along with actionable data and a feedback system that track the outcome produced by action taken.

The present disclosure provides an artificial intelligence-based system configured to manage the health and care of a person in an extended healthcare community. In some embodiments, a member of a healthcare community may include, but is not limited to, any of a physician, a nurse, a registered nurse, a nurse practitioner, a physician assistant, an emergency medical technician, an ambulance or an ambulance operator, a clinic, a hospital, a skilled nursing facility (SNF), a home care or home health agency, a patient, a family member of a patient, a friend of a patient, a care taker of a patient, an insurance provider, an employer of a patient, or any other stakeholder.

In some embodiments, such as illustrated in FIG. 7, systems collect healthcare data. Healthcare data may be collected from other systems of using other methods. In various embodiments, healthcare data may include, but is not limited to, any of clinical data from electronic health records (EHR), clinical data in HL7 or other formats from other clinical systems, for example, lab, radiology, or others, claim data from insurers, socio-economic data, patient-reported data, diagnostic and home-based device data, claim data from Centers for Medicare and Medicaid Services (CMS), claim data from commercial payors, any other financial or clinical data, or administrative data.

According to some embodiments, systems may support a data set including at least the full HL7 v3 Clinical Document Architecture (CDA) and all of the data acquired and/or collected by health insurers, including the Centers for Medicare and Medicaid Services (CMS) and commercial insurers, patient reported data, device data such as home, clinic, hospital, or other devices, as well as all the socio-economic data available directly or that collected and/or stored by commercial data aggregators such as Lexis-Nexis.

According to some embodiments, a system may comprise strata, including a user interface, artificial intelligence layers, and a data warehouse.

Aspects of the disclosure provide artificial intelligence layers. In some embodiments, artificial intelligence layers and application of the artificial intelligence layers is controlled by a set of foundational concepts. In some embodiments, foundational concepts may act as an axis that runs through the system According to various embodiments, artificial intelligence layers may include but are not limited to, any of foundational concepts, a knowledge layer, a service layer, a clinical decision support layer, a documentation layer, an analytics layer, or an administrative layer, for example, for billing and reimbursement.

Artificial intelligence layers may be arranged in various orders. For example, artificial intelligence layer order may be different based on different foundational concepts. In some embodiments, two important foundational concepts are clinical concepts and value driven concepts.

In some embodiments, a clinical concept may be simple. For example, a clinical concept may be based on one clinical parameter, such as a diagnosis of congestive heart failure (CHF). In other embodiments, a clinical concept may be complex. For example, a clinical concept may have multiple clinical attributes, for example, pharmacogenomics (PGx), for all those patients who have a disease that requires pharmacogenomics testing, and are on a medication that requires pharmacogenomics testing, and/or risk factors that may require pharmacogenomics testing. According to various embodiments, clinical concepts may be single or combinations of any of, but not limited to, problems, diseases, labs, results, procedures, investigations, treatment protocols, medications, risk factors, prognosis, or assessments.

In some embodiments, a value driven concept may be based on payer or provider-based initiatives and programs. In some embodiments, a value driven concept may be based on certain well-defined programs from payers, employers, or providers. Examples of value driven concepts include value-based programs such as any of ACOs, Medicare Advantage, or bundled payment programs. In addition, value driven concepts may include payer, employer, or provider initiatives, for example, smoking cessation. In some embodiments, value driven concepts may include a patient driven program, or a quality measure driven program. All Filters allow selection of an appropriate foundational concept to load data from all layers into a program matrix. Other examples of foundational concepts include, but are not limited to AWV, CCM, TCM, PCM, BPCI, MIPS, CPIA, QPP, CJR, PGx, BPCI, ACO, HEDIS, Readmit 90, Readmit 30. At one time, one or more program matrices may be loaded onto a system.

After a foundational concept is selected. appropriate data elements, knowledge concepts, service elements, decision support alerts and actions, documentation layer, analytics and administrative components are preselected and loaded into a system and used to define a program matrix. For example, the two exemplary foundational concepts, clinical concepts and value driven concepts, may act as a central axis. When the foundational concepts shift, the program matrix may also shift and change. The central axis runs through all layers in the matrix. High complexity nodes may be identified where artificial intelligence can improve care or ease the burden of a care provider.

According to various embodiments, nodes may include, but are not limited to, any of eligibility, risk stratification, care gaps, assessments, services, quality measures, care plans, or administrative and billing.

Inputs to nodes may be derived from the various layers. The nodes may comprise decision points in the workflow where a system is configured to use captured patient healthcare data to apply a rules engine or a trained statistical model, for example, a trained statistical model derived through machine learning algorithms, and provide actionable information independent of the platform or the modules. Providing this artificial intelligence layer independent of the platform and or the modules allows for greater ease and flexibility in creating custom programs without any additional programming.

A system may include a foundational concept program axis. In some embodiments, the foundational concept program axis layer may serve as a central axis and may be configured to define which element from each of the frames or layers are activated to define a program matrix. The order or hierarchy of each element may be predefined. For example, if a provider creates a program based on BPCI-A, the program axis may be set to BPCI-A. The other six layers may be arranged to reflect a foundational concept program axis selection.

A system may include a knowledge layer. In some embodiments, a knowledge layer may be configured to define knowledge parameters of a program including eligibility rules, inclusion and exclusion logic based on payer, program and calendar year, patient demographics, clinical conditions based on structured and unstructured data in the CCDs, HL 7, Flat Files, QRDA, or other data. For example, for BPCI-A eligibility, rules may be set to Medicare Part A and B with an appropriate set of diagnoses captured through DRGs. In some embodiments, a knowledge layer may identify an appropriate rule set for clinical, quality, and financial interventions. In the example, clinical interventions may be identified based on BPCI-A needs and may include certain post discharge follow up instructions, health literacy, appropriate tests such as LVEF for CHF, appropriate Medications. In some embodiments, a risk score calculation at the time of discharge may be included in a BPCI program A system may include a service layer. In some embodiments, a service layer may be configured to determine which services will be made available based on a program. For example, services may include, but are not limited to, any of post discharge follow up, monthly calls, weekly follow ups. In the exemplary case of BPCI-A, providers may offer TCM and care management services to patients.

A system may include a CDS Layer. In some embodiments, a CDS layer may be configured to display alerts and recommendations which are relevant to a program. Alerts or recommendation may be clinical, quality, or financial in nature. In the example of BPCI, quality CDS alerts and intervention may be focused on Advanced Care Plan and 30 days readmission. In some embodiments, clinical alerts and guidelines may be configured to provide appropriate care for a patient based on evidence-based guidelines. In some embodiments, a CDS layer may be configured to suggest assessments based on a patient diagnosis and based on current healthcare data. For example, BPCI assessments for a CHF patient may focus on recent discharge, CHF literacy, symptom control, symptomatic care, and medication management. As another example, daily weights, weight gain monitoring, and other weight related data may be configured by a CDS layer.

According to various embodiments, a CDS layer may utilize both the rule-based suggestions as well as suggestions based on trained statistical models, for example, machine learning algorithms. A program may use either rule-based or suggestions based on trained statistical models, for example, machine-based suggestions to provide decision support. According to one exemplary embodiment, a machine-based algorithm comprises machine learning predictions. For example, a cohort of predictive set of patients with COVID 19 may be built using a machine learning-based prediction using the machine learning algorithms described herein. Machine learning algorithms may be built using training data sets and test sets.

A system may comprise a documentation layer. According to some embodiments, a documentation layer may configure documentation that will improve a program. A documentation layer may be configured to generate alerts when documentation criteria are met. A documentation layer may help providers better document patient conditions for certain conditions as well as capture information from the longitudinal record of a patient to populate forms so that provider do not have to review questions that may be redundant. For the BPCI example, appropriate documentation may be CQMs and PSI, which may impact BPCI A payments. In some embodiments, a documentation layer may generate a discharge summary. In some embodiments, a documentation layer may generate documentation of which PAC a patient is discharged to.

A system may include an analytics layer. An analytics layer may be configured to determine information that will be displayed in an analytics area and a scorecard for enterprise, practice, and providers. For the BPCI example, the analytics layer may show a monthly CQM compliance, a number of BPCI patients in each DRG, care management, transition of care follow up, readmissions, LOS, GMLOS within acute and post-acute settings, and other information.

A system may include an administrative layer. In some embodiments, an administrative layer may configure billing and reimbursement components. An administrative layer may be configured to gather billing codes applicable to a program and prepare a billing report for those billing codes.

For the BPCI example, any billing codes which are applicable in the service of BPCI A patients are captured and gathered in a billing report.

Aspects of the disclosure provide an artificial intelligence engine. In some embodiments, an artificial intelligence engine supports and enables the each of the layers of the artificial intelligence layers strata. An artificial intelligence engine may support artificial layers by performing several functions. One of the functions may include sorting through collected data from all sources and performing semantic and structural normalization. Another function of the artificial intelligence engine may include using rules as well as trained statistical models, such as models generated by machine learning, to operate off of evidence-based knowledge and the collected data. For example, using the rules and trained statistical models may include analyzing current healthcare data to identify any events associated with the healthcare data to determine if an alert for the event should be generated for a stakeholder. Using the rules and trained statistical models may also include determining the content of the alert. Using the rules and trained statistical mode may include determine what, if any data, action recommendations, protocols or alerts, as well as the order and modality of these events, should be presented to a stakeholder, depending on the role and preference of the stakeholder.

According to various aspects, an artificial intelligence engine may use a combination of at least one of a semantic rules engine or a probabilistic graphical model (PGM) engine. In some embodiments, the artificial intelligence engine may use the at least one of the semantic rules engine or the PGM to determine what information to present to a user such as a healthcare professional. The artificial intelligence engine may further use the at least one of the semantic rules engine or the PGM to determine how to present the information to the healthcare professional at any point in time. The artificial intelligence engine may be programmed to continuously analyze all new healthcare data as the new healthcare data becomes available, and to integrate the new healthcare data into the existing healthcare data to determine what, if any, new healthcare events may be generated. In some embodiments, the artificial intelligence engine may generate healthcare events such as information, alerts, guidelines, protocols, or actions that are to be recommended and/or presented to a user such as a healthcare professional.

An artificial intelligence engine may include various events, for example, thousands of events, that may form a series of Bayesian network directed graphical models. For example, when an artificial intelligence engine detects that there is new healthcare data associated with a patient, the artificial intelligence engine may run the patient record through a rules engine and the PGM engine. The rules engine and the PGM engine may produce a set of results. The set of results may include healthcare events such as evidence based alerts, guidelines, and protocols to be presented to specific stakeholders based on their role, as well as specific sections of a patient record to be presented to specific stakeholders based on their role. The system may format these sections may be formatted according to the layout section. FIGS. 9A-9D show one embodiment of a GUI for providing rules of a statistical model.

Aspects of the disclosure provide a measure builder. A measure builder may be configured to use an artificial intelligence engine to detect healthcare events and perform a series of one or more actions based on the detected events.

A measure builder may be configured to allow users to use a cohort builder to dynamically create a cohort of patients. A measure builder may be configured to allow users to create specific user interface views using key clinical, socio-economic, behavioral, spend and utilization key performance indicators (KPIs) from a predefined list of such KPIs, for example, a KPI Library, for the population or for the individual patients in that population create a dynamic view that allows a user to further drilldown into aspects of the user interface. Events may provide the information layouts described herein.

According to some embodiments, a cohort builder may use a semantics artificial intelligence engine. A cohort builder may be configured to allow users to select rules or queries from a library of rules and queries or top create new healthcare events to define a denominator population and define a numerator population. For both the denominator and numerator healthcare events, the system allows a user to select any combination of demographic, clinical, claims and process datums chosen from a flexible library of datums. According to various embodiments, datums may include attributes and variables. In some embodiments, datums define events. For example, a healthcare event could consist of datums including a diagnosis of a patient, vital signs of a patient, lab values of a patient, and insurance and service line of a patient.

Attributes of a datum may comprise the various elements that a datum needs. For example, the attributes of vital signs may include, but are not limited to, temperature, pulse, blood oxygen level of a patient. Variables of a datum may comprise text and codes from various vocabularies, terminologies and standards that are used to define the data being acquired and processed. For example, a variable may be used to define a diagnosis of diabetes. This exemplary variable may contain a list of all the ICD9, ICD10, and SNOMED, or other codes used to refer to diabetes. Using a variable allows the system to capture the fact that a patient has diabetes irrespective of how that fact may have been coded in any of the systems from which the instant system receiving the healthcare data associated with a patient.

The system allows users to define datum and attribute values and/or rates of change of these variables in each rule. In some embodiments, rules and queries may be created manually by a user. In some embodiments, a system may use a combination of trained statistical modes, such as machine learning algorithms, to create rules and queries that identify populations of patients or individual patents that are most in need of interventions. In some embodiments, a need may be associated with undesirable results from any combination of clinical, genetic, socio-economic, behavioral, financial, utilization, or other factors. FIGS. 12A-12D show one embodiment of a GUI for providing rules of a statistical model.

A system may provide a key performance indicator (KPI) library. The system may allow users to select particular KPIs from a library of KPIs. The KPIs may be applied to an entire cohort of patients or to an individual patient.

In some embodiments, KPIs may include, but are not limited to per member per month (PMPM) costs, risk scores such as HCC score, SSR score, or social determinants of care (SDOH) score, spend and utilization of inpatient, outpatient or part B, emergency room (ER) visits, lab, radiology, magnetic resonance imaging (MRI), medication, skilled nursing facility (SNF) home health, length of stay, demographic measures such as number of new patients and changes to the existing patient population in each program from one period to the next, which physicians served these patients, which physician had the best or worst performance, costs comparisons to averages and to benchmarks, risk and spend distribution of these patients, which clinical factors a provider should be aware of either from a clinical or spend impact point of view, for example, diagnoses, dialysis, aged, clinical quality measures (CQM) such as which CQMs apply to this population and what are their scores, what are the scores of each provider serving this patient or population, either an overall score or a score for this population.

Figure 10:
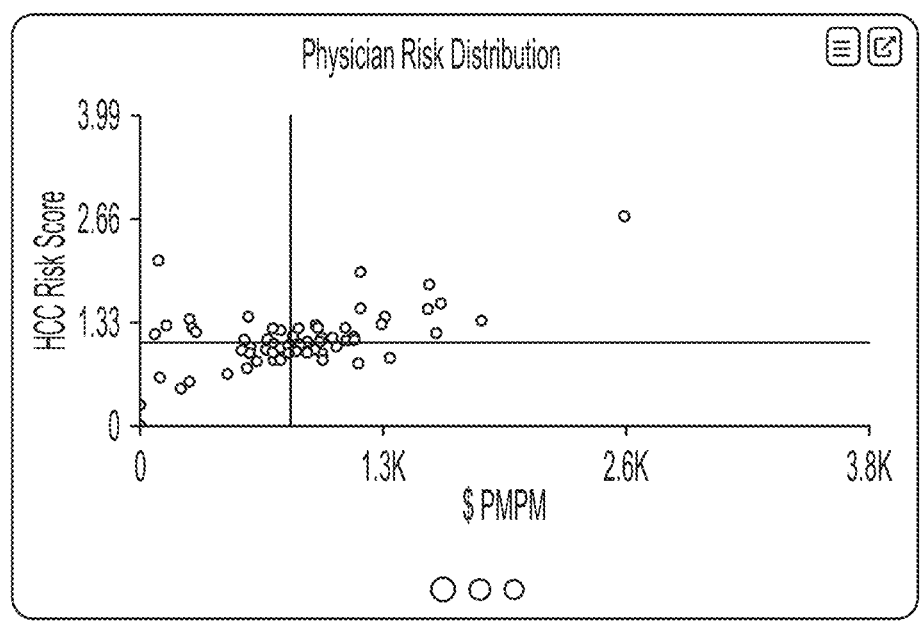
FIG. 10 shows one embodiment of displaying risk scoring trends.
Figure 12B:
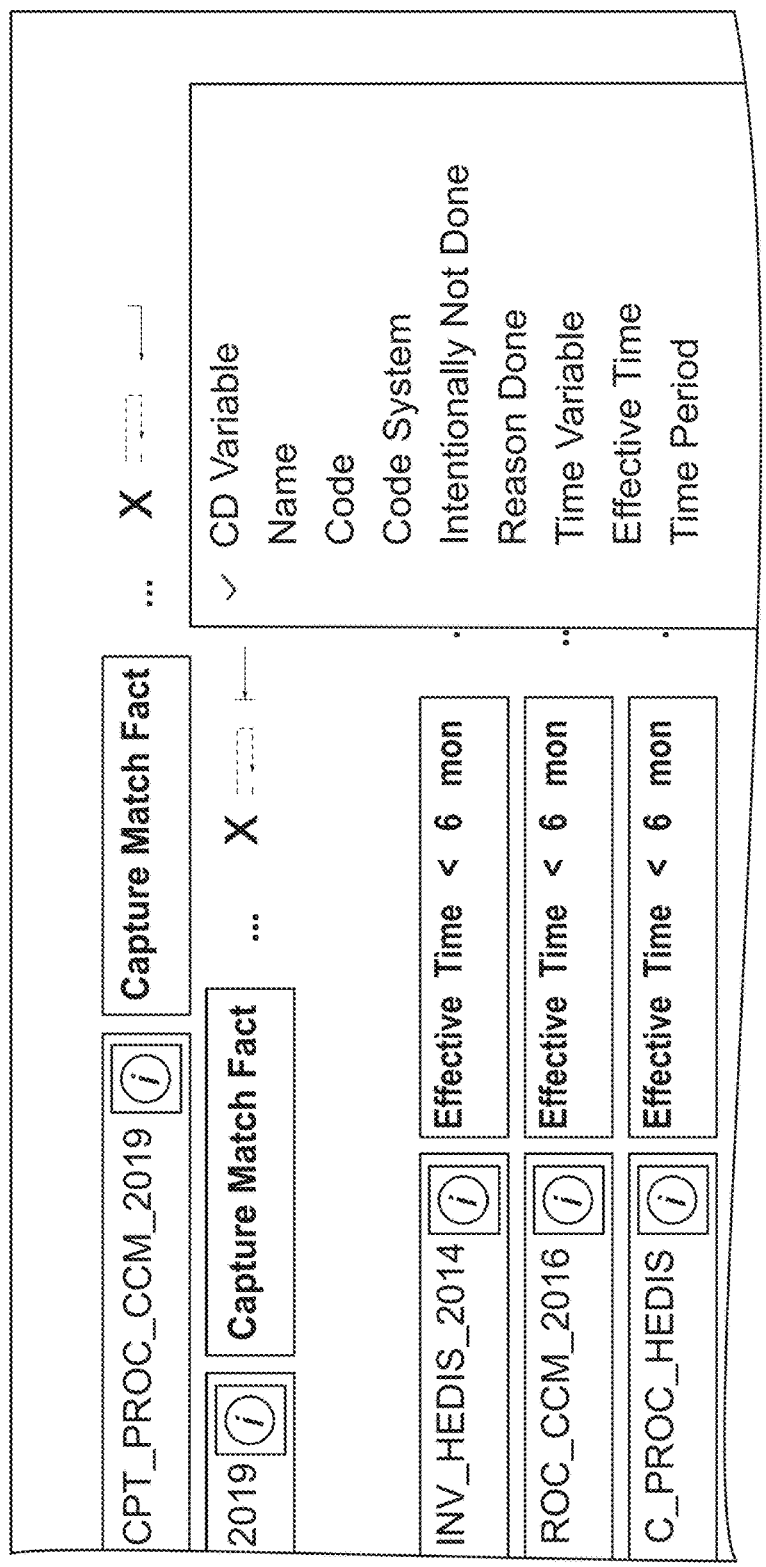
Figure 13:
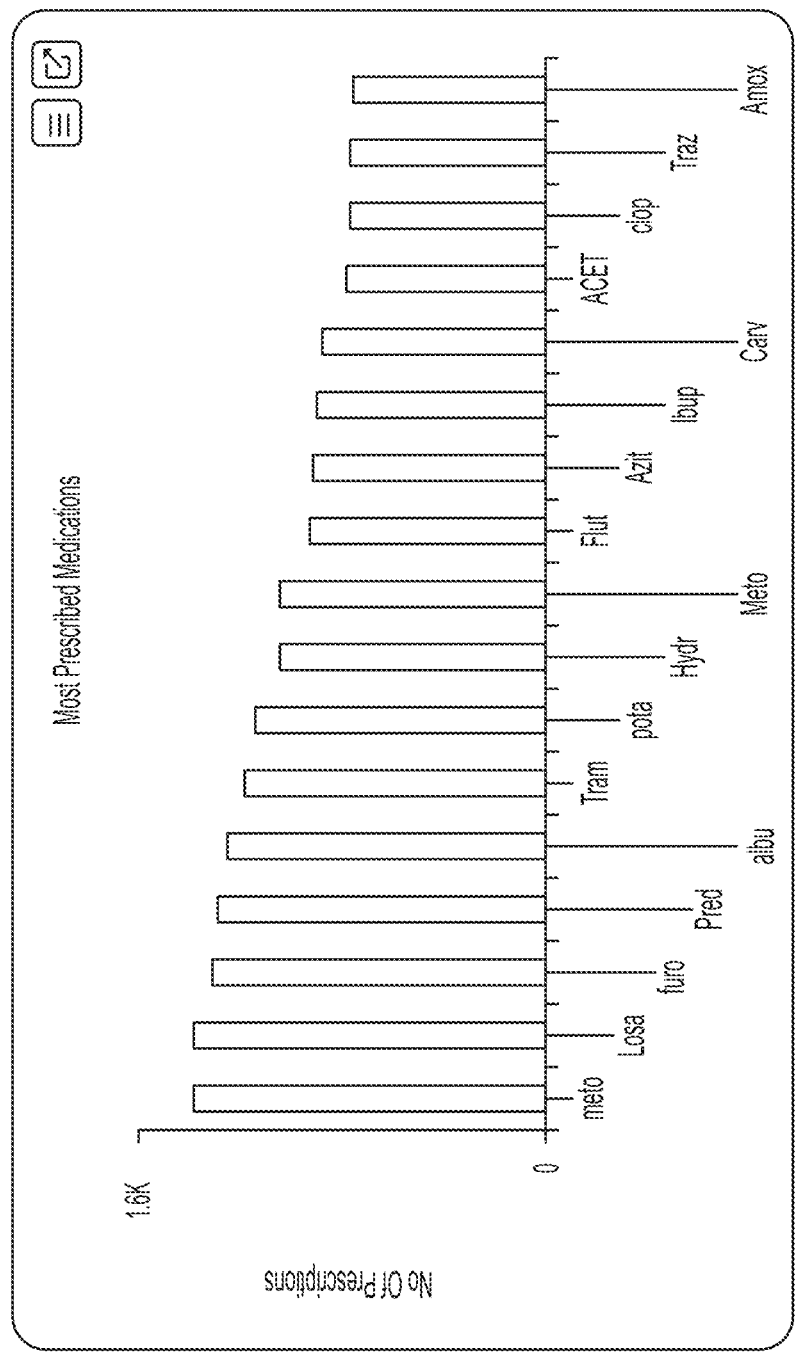
FIG. 13 shows one embodiment of displaying medication prescription trends.

For example, FIG. 10 shows one embodiment of displaying trends of a distribution of risk score compared to per member per month (PMPM) cost. FIG. 11 shows one embodiment of displaying trends related to quality, cost, and utilization information for patients. FIG. 13 shows an exemplary embodiment of displaying medication prescription trends for patients. FIG. 14 shows an exemplary embodiment of care opportunity trends for various programs, including monthly and yearly performance compared to performance targets.

A system may provide additional information associated with a particular KPI. For example, the system may provide KPIs that allow a user to drilldown and expose an exact path an associated rule took to be triggered.

Aspects of the disclosure provide a data layer. A data layer may be configured to provide data acquisition, aggregation, semantic normalization, ingestion, transformation, and display.

A data layer may be configured to collect data from various sources that might contain relevant data about a patient. According to various embodiments, sources that might contain relevant data about a patient may include, but are not limited to, any of clinical data from one or more electronic health record (EHR), hospital data, HL7, including admissions, discharge and transfer (ADT) data, claim data from one or more sources, patient-reported data, device data such as home device data, social determinants of health data, economic or spending data, or other relevant data.

A data layer may be configured to perform semantic normalization by transforming coding of acquired data into standard codes that can then be used to create a single longitudinal record for each patient. A single record for a patient may be used by artificial intelligence strata to perform any of the functions described herein.

After a foundational concept has been selected, artificial intelligence strata may then determine which elements of a patient record are relevant. An element of a patient record may be determined to be relevant when it might impact the program matrix. For the BPCI example, data fields that may be important for BPCI but may not be important for other programs may include, but are not limited to, length of stay (LOS), geometric mean length of stay (GMLOS), discharge disposition, skilled nursing facility (SNF) location, SNF LOS, SNF GMLOS, home health (HH) LOS, HH GMLOS. For example, admit and discharge dates for inpatient stay and ER and observation stays may be ignored because they are in the BPCI program. In the example, a first stay in a program year is termed an anchor stay and may determine the episode and its expenditure post discharge for a ninety-day period. In the example, all data may be collected for every patient for ninety days post discharge after which the episode is automatically terminated. In some embodiments, all clinical data including occupation therapy and physical therapy notes may be included for a program.

Example: BPCIA Program

According to one example, a hospital system is participating in the Bundled Payment for Clinical Improvement—Advanced (BPCIA) program. A foundational concept in this example is BPCI, which defines a program matrix based on the BPCI Advanced initiative by Medicare. The BPCI Program Matrix has a concept of Conveners and Episode Initiators (EI). The hospital system is referred to as the Convener and is the entity that has the risk sharing contract with CMS. The individual hospitals are referred to as the EIs and each hospital is the entity that signs up under the Convener to manage the care of patients that may have certain episodes. According to the example, Hospital 1, which is an EI, may be enrolled in Chronic Heart Failure (CHF) and COPD episodes and Hospital 2 may be enrolled in in AMI and Cardiac Arrythmia episodes.

After the foundational concept has been selected, the artificial intelligence strata described herein then determine the eligibility of each patient that is admitted to either of the two hospitals to see if that patient qualifies to be in one of the episodes.

After the eligibility of a patient has been determined, the artificial intelligence strata may identify appropriate elements of the patient's nodes. For example, some elements of a patient's nodes may include a risk score, which quality measures should be monitored, which assessments should be performed, which care gaps are to be filled, which billable or non-billable services should be performed. The artificial intelligence strata may also create a personalized care plan based on the above nodes. The artificial intelligence strata may also generate any tasks and goals for the patient that should be achieved by the patient or by members of a care team. The artificial intelligence strata may also create any billing reports. The artificial intelligence strata may also assign a priority to each of the elements above. Priority information may be used by the artificial intelligence to generate any of the user interfaces or user experiences described herein.

Figure 8:
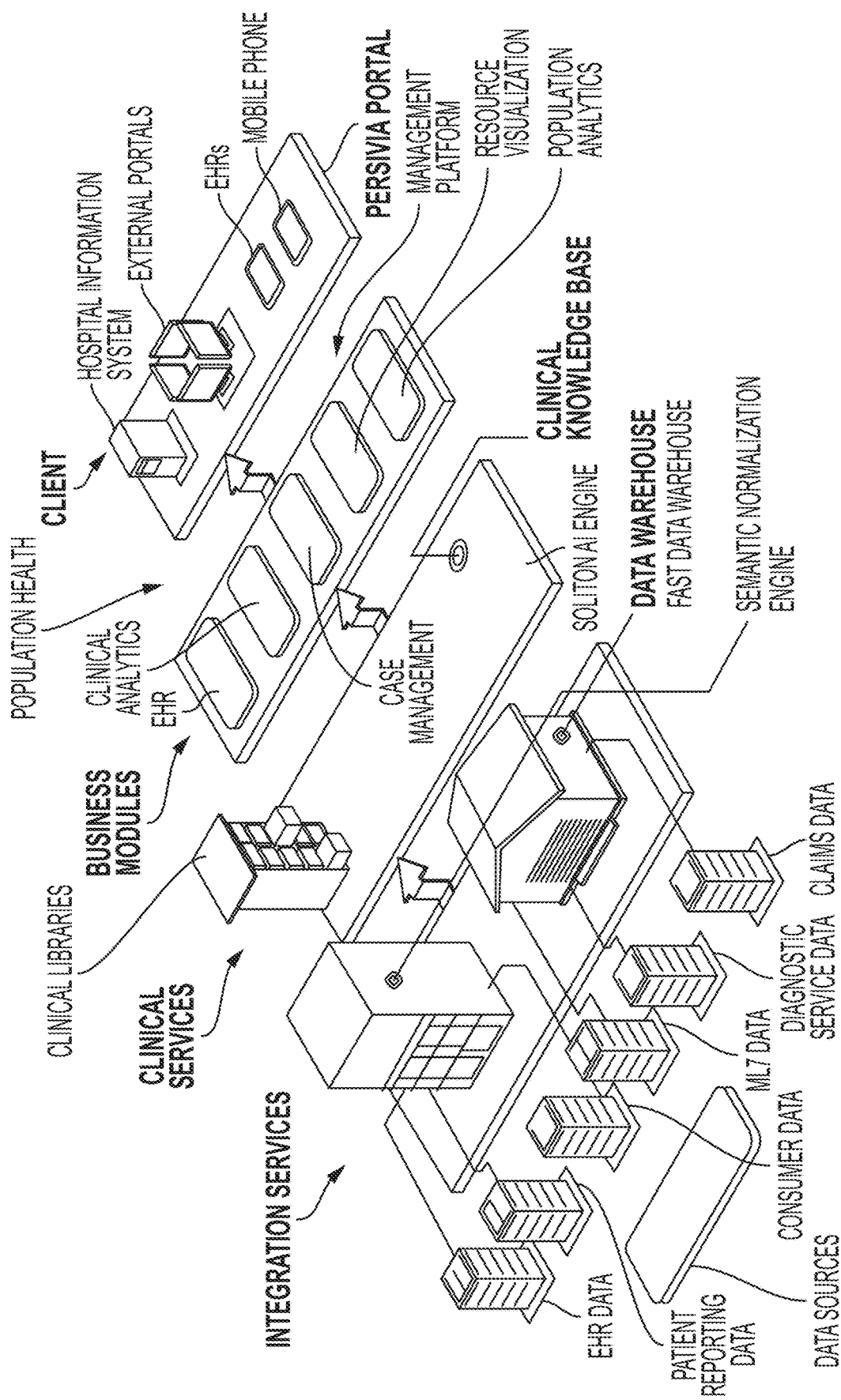
FIG. 8 shows one embodiment of a system for providing a workflow of a healthcare professional.
Figure 9B:
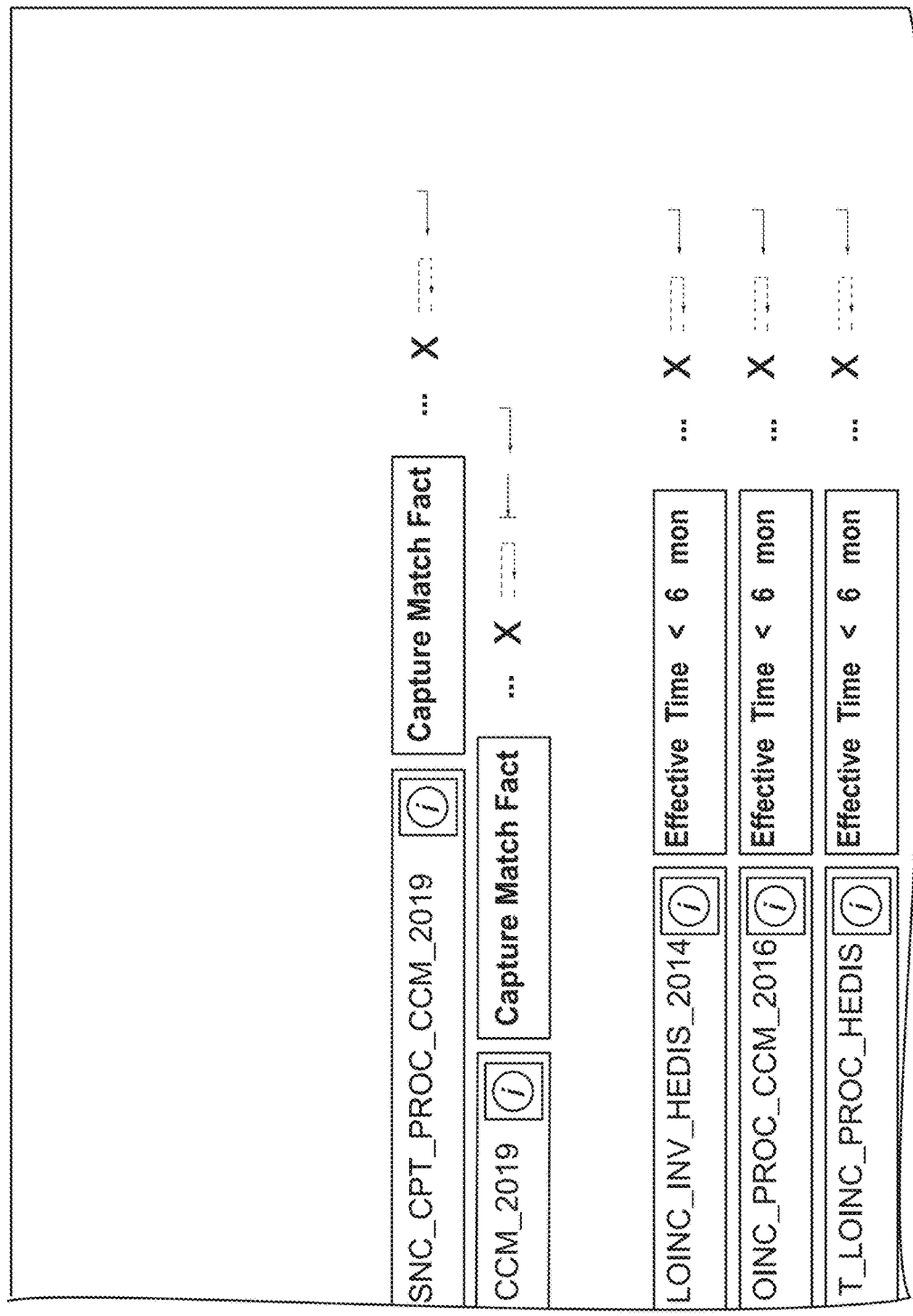
Figure 9D:
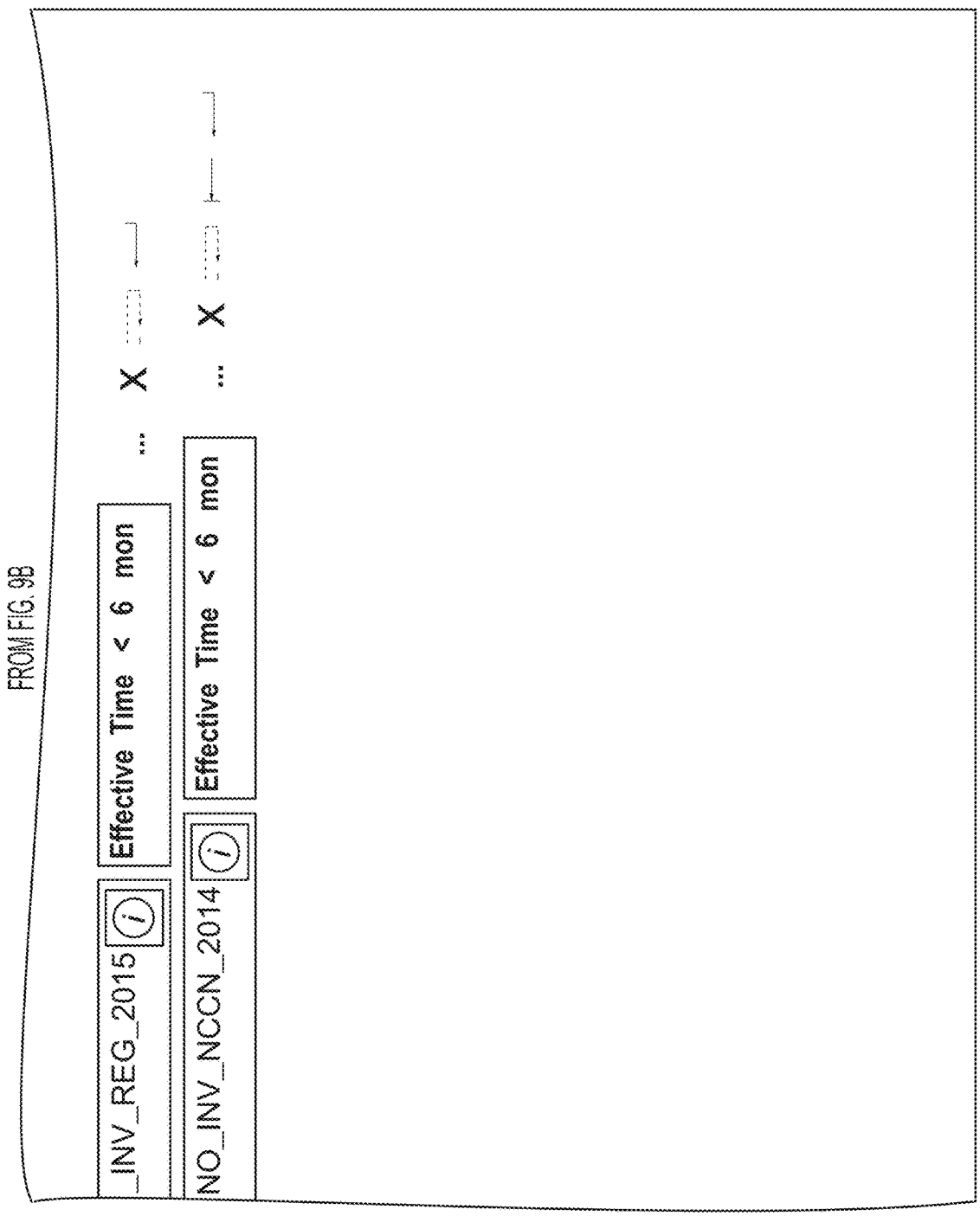
Figure 15:
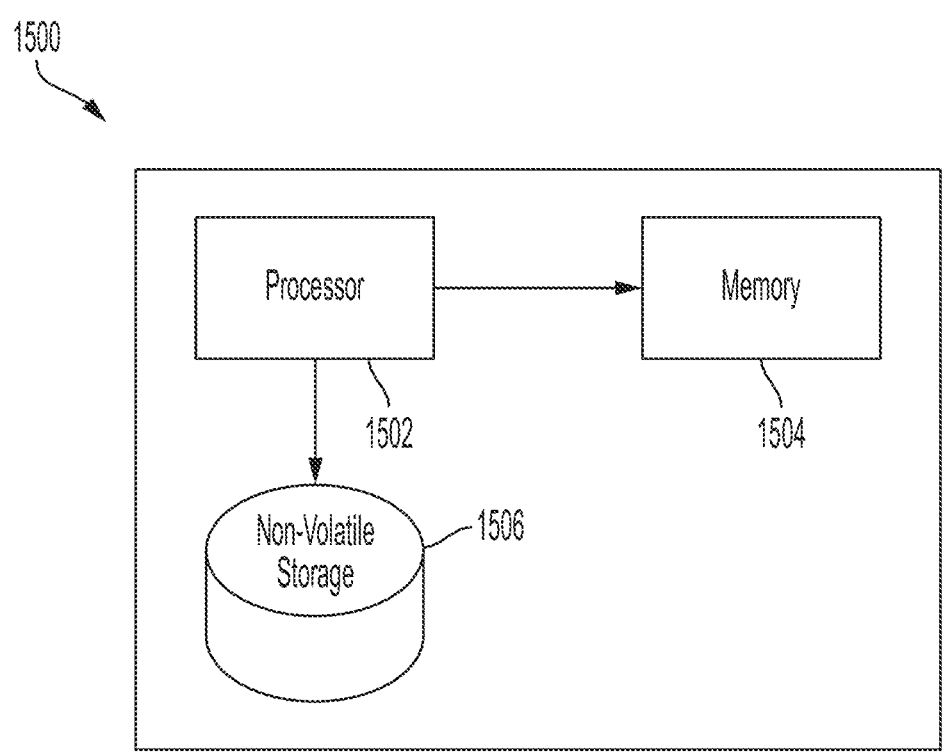
FIG. 15 is a block diagram of a computer system on which various functions can be implemented.

An illustrative implementation of a computer system 1500 that may be used in connection with any of the embodiments of the disclosure provided herein is shown in FIG. 15. The computer system 1500 may include one or more processors 1502 and one or more articles of manufacture that comprise non-transitory computer-readable storage media, for example, memory 1504 and one or more non-volatile storage media 1506. The processor 1502 may control writing data to and reading data from the memory 1504 and the non-volatile storage device 1506 in any suitable manner. To perform any of the functionality or methods described herein, for example, process 100 or process 200, the processor 1502 may execute one or more processor-executable instructions stored in one or more non-transitory computer-readable storage media, for example the memory 1504, which may serve as non-transitory computer-readable storage media storing processor-executable instructions for execution by the processor 1502. Alternatively or additionally, any of the functionality or methods described herein may be performed by a system such as the system illustrated in FIG. 8.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

The terms "approximately," "substantially," and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

In view of the described embodiments of the techniques described herein and variations thereof, below are described certain more particularly described aspects. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A system that manages the healthcare of a person comprising:
a user interface;
artificial intelligence layers; and
a data warehouse.

Aspect 2: The system of aspect 1 wherein the system collects at least some of the following data: clinical data from electronic health records, clinical data from the other clinical systems (lab, radiology etc.), claims data from insurers, socio-economic data, patient reported data, diagnostic and/or home based device data, claims data from CMS, claims data from commercial payers, financial data, and administrative data.

Aspect 3: The system of aspect 1 or 2 wherein the artificial intelligence layers include at least one of a foundational concepts layer, a knowledge layer, a service layer, a clinical decision support layer, a documentation layer, an analytic layer, and an administrative layer.

Aspect 4: The system of aspect 3 wherein the artificial intelligence layers include at least one of a semantic rules engine and a probabilistic graphical model engine and apply clinical concepts and value driven concepts.

Aspect 5: The system of aspect 1 wherein the user interface displays information dependent upon workflow being carried out by the artificial intelligence layers.

Aspect 6: The system of aspect 5 wherein the user interface has a patient page and a provider page.

Aspect 7: A system comprising:
a data acquisition module that acquires data;
a data preparation module that receives and prepares the acquired data;
an expert system module that applies evidenced based rules to the prepared data;

a data discovery module that utilizes at least one of unsupervised and semi-supervised machine learning algorithms to guide the application of evidenced based rules to the prepared data;
an analytics module that applies analytics to the data; and
an output module that provides at least one of a report, display and an alert.

Aspect 8: The system of aspect 7 wherein the data acquisition module includes at least one of real time acquisition and batch acquisition.

Aspect 9: The system of aspect 7 wherein the data preparation module includes at least one of data enrichment, data normalization, data aggregation and data translation.

Aspect 10: The system of aspect 7 wherein the analytics module applies at least one of prescriptive analytics, descriptive analytics, and predictive analytics.

Aspect 11: The system of aspect 7 wherein the data includes at least one of data from an EHR, a clinical system, a health and/or financial and/or insurance claim, a socio-economic report, a patient report, and a doctor report.

Aspect 12: A method comprising:
acquiring data;
preparing the acquired data;
applying evidenced based rules to the acquired data;
using at least one of unsupervised and semi-supervised machine learning algorithms to guide the application of evidence based rules to the prepared data;
applying analytics to the data; and
providing an output.

Aspect 13: The method of aspect 12 wherein acquiring the data includes at least one of real time acquiring and batch acquiring.

Aspect 14: The method of aspect 12 wherein preparing the data includes applying to the data at least one of data enrichment, data normalization, data aggregation and data translation.

Aspect 15: The method of aspect 12 wherein applying the analytics includes applying at least one of prescriptive analytics, descriptive analytics, and predictive analytics.

Aspect 16: The method of aspect 12 wherein the data includes at least one of data from an EHR, a clinical system, a health and/or financial and/or insurance claim, a socio-economic report, a patient report, and a doctor report.

Aspect 17: The method of aspect 12 wherein providing the output includes providing at least one of a report, a display and an alert.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method comprising:
receiving, by at least one computer processor, healthcare data comprising electronic healthcare records associated with a plurality of patients of a healthcare professional, the plurality of patients including a first patient and a second patient;
preparing, by the at least one computer processor, the electronic healthcare records with a consistent computer data structure configured for inputting to a trained statistical model, the electronic healthcare records including healthcare codes for the plurality of patients belonging to a plurality of different medical classification standards, wherein preparing the electronic healthcare records with the consistent computer data structure comprises:
transforming, by the at least one computer processor, the electronic healthcare records, from a plurality of differently-structured data formats into the consistent computer data structure, wherein an operation to perform the transforming includes one or more of:
an aggregation operation configured to identify a plurality of entities associated with the electronic healthcare records of differently-structured data formats and compile a plurality of data feeds for the plurality of entities into a common consolidated entity;
a normalization operation configured to reduce data redundancy across the plurality of data feeds for the plurality of entities; or
an enrichment operation configured to identify and add curated electronic healthcare records of the plurality of differently-structured data formats from the plurality of data feeds for the plurality of entities, into a record formatted according to the consistent computer data structure;
validating, by the at least one computer processor, that the electronic healthcare records conform to the consistent computer data structure, wherein the consistent computer data structure is configured for use with at least one of a foundational concept data operation, a knowledge data operation, a service data operation, a clinical decision support data operation, a documentation data operation, an analytics data operation, or an administrative data operation;
inputting, by the at least one computer processor, to the trained statistical model, the electronic healthcare records prepared with the consistent computer data structure, wherein the trained statistical model is trained on training data comprising, for each diagnosis of a plurality of diagnoses:
a respective variable; and
linked with the respective variable, a set of healthcare codes corresponding to each medical classification standards of the plurality of different medical classification standards, wherein:
each healthcare code of the set of healthcare codes corresponds to the diagnosis;
surfacing, by the at least one computer processor, using the trained statistical model, at least one hidden relationship between the electronic healthcare records with the consistent computer data structure and at least one clinical intervention and encoding the at least one hidden relationship as an explicit value in the consistent computer data structure;
generating, by the at least one computer processor, a workflow of the healthcare professional using an output of the trained statistical model calculated based on the electronic healthcare records prepared with the consistent computer data structure, the output of the trained statistical model comprising the at least one hidden relationship between the electronic healthcare records with the consistent computer data structure and the at least one clinical intervention, wherein the workflow of the healthcare professional comprises:
one ordered list of a plurality of healthcare events for the healthcare professional prompting the healthcare professional to provide care to the first patient and provide care to the second patient after providing care to the first patient; and within the one ordered list, a first healthcare event specific to the first patient and a second healthcare event specific to the second patient, the first healthcare event and the second healthcare event being ordered with respect to each other within the workflow, wherein:
the prompting to provide care to the second patient after providing care to the first patient is generated based on the surfaced at least one hidden relationship between the electronic healthcare records with the consistent computer data structure and the at least one clinical intervention and using the healthcare codes belonging to the plurality of different medical classification standards;
providing, via a display, a graphical user interface (GUI) representing the workflow of the healthcare professional, the GUI comprising a plurality of GUI elements representing respective healthcare events of the plurality of healthcare events; and
continuously updating, by the at least one computer processor, the workflow of the healthcare professional based on subsequent outputs of the trained statistical model calculated based on the electronic healthcare records prepared with the consistent computer data structure and based on updated healthcare codes for the plurality of patients belonging to the plurality of different medical classification standards; and
automatically moving, based on the continuously updated workflow of the healthcare professional, positions, within the GUI provided via the display, of the plurality of GUI elements representing the respective healthcare events, so as to provide the healthcare professional with continuously updated prompts to interact with the plurality of patients.

2. The method of claim 1, wherein the plurality of healthcare events comprises at least one of a task, an alert, or an appointment request for the healthcare professional.

3. The method of claim 1, wherein the trained statistical model is configured to provide the output based on at least one of time, criticality, or clinical evidence associated with the healthcare data.

4. The method of claim 1, further comprising prompting the healthcare professional to follow up with the first patient of the plurality of patients.

5. The method of claim 4, wherein the prompting the healthcare professional to follow up is performed based on a location of the healthcare professional.

6. The method of claim 1, further comprising:
providing, in the workflow, in the first healthcare event of the plurality of healthcare events, an indication of the first patient of the plurality of patients; and
in response to a selection of the indication of the first patient, providing, to the healthcare professional, a profile of the first patient.

7. The method of claim 1, wherein the healthcare data comprises financial data.

8. At least one non-transitory computer-readable storage medium having instructions encoded thereon that, when executed by at least one computer processor, cause the at least one computer processor to perform a method comprising:
receiving healthcare data comprising electronic healthcare records associated with a plurality of patients of a healthcare professional, the plurality of patients comprising a first patient and a second patient;
preparing the electronic healthcare records with a consistent computer data structure configured for inputting to a trained statistical model, the electronic healthcare records including healthcare codes for the plurality of patients belonging to a plurality of different medical classification standards, wherein preparing the electronic healthcare records with the consistent computer data structure comprises:
transforming, by the at least one computer processor, the electronic healthcare records, from a plurality of differently-structured data formats into the consistent computer data structure, wherein an operation to perform the transforming includes one or more of:
an aggregation operation configured to identify a plurality of entities associated with the electronic healthcare records of differently-structured data formats and compile a plurality of data feeds for the plurality of entities into a common consolidated entity;
a normalization operation configured to reduce data redundancy across the plurality of data feeds for the plurality of entities; or
an enrichment operation configured to identify and add curated electronic healthcare records of the plurality of differently-structured data formats from the plurality of data feeds for the plurality of entities, into a record formatted according to the consistent computer data structure;
validating, by the at least one computer processor, that the electronic healthcare records conform to the consistent computer data structure, wherein the consistent computer data structure is configured for use with at least one of a foundational concept data operation, a knowledge data operation, a service data operation, a clinical decision support data operation, a documentation data operation, an analytics data operation, or an administrative data operation;
inputting, to the trained statistical model, the electronic healthcare records prepared with the consistent computer data structure, wherein the trained statistical model is trained on training data comprising, for each diagnosis of a plurality of diagnoses:
a respective variable; and
linked with the respective variable, a set of healthcare codes corresponding to each medical classification standard of the plurality of different medical classification standards, wherein:
each healthcare code of the set of healthcare codes corresponds to the diagnosis;
surfacing, by the at least one computer processor, using the trained statistical model, at least one hidden relationship between the electronic healthcare records with the consistent computer data structure and at least one clinical intervention and encoding the at least one hidden relationship as an explicit value in the consistent computer data structure;
generating a workflow of the healthcare professional using an output of the trained statistical model calculated based on the electronic healthcare records prepared with the consistent computer data structure, the output of the trained statistical model comprising the at least one hidden relationship between the electronic healthcare records with the consistent computer data structure and the at least one clinical intervention, wherein the workflow of the healthcare professional comprises:
one ordered list of a plurality of healthcare events for the healthcare professional prompting the healthcare professional to provide care to the first patient and provide care to the second patient after providing care to the first patient; and within the one ordered list, a first healthcare event specific to the first patient and a second healthcare event specific to the second patient, the first healthcare event and the second healthcare event being ordered with respect to each other within the workflow, wherein:

the prompting to provide care to the second patient after providing care to the first patient is generated based on the surfaced at least one hidden relationship between the electronic healthcare records with the consistent computer data structure and the at least one clinical intervention and using the healthcare codes belonging to the plurality of different medical classification standards;

providing, via a display, a graphical user interface (GUI) representing the workflow of the healthcare professional, the GUI comprising a plurality of GUI elements representing respective healthcare events of the plurality of healthcare events; and continuously updating the workflow of the healthcare professional based on subsequent outputs of the trained statistical model calculated based on the electronic healthcare records prepared with the consistent computer data structure and based on updated healthcare codes for the plurality of patients belonging to the plurality of different medical classification standards; and automatically moving, based on the continuously updated workflow of the healthcare professional, positions, within the GUI provided via the display, of the plurality of GUI elements representing the respective healthcare events, to provide the healthcare professional with continuously updated prompts to interact with the plurality of patients.

9. The at least one non-transitory computer-readable storage medium of claim 8, wherein the plurality of healthcare events comprises at least one of a task, an alert, or an appointment request for the healthcare professional.

10. The at least one non-transitory computer-readable storage medium of claim 8, wherein the trained statistical model is configured to provide the output based on at least one of time, criticality, or clinical evidence associated with the healthcare data.

11. The at least one non-transitory computer-readable storage medium of claim 8, wherein the method further comprises prompting the healthcare professional to follow up with the first patient of the plurality of patients.

12. The at least one non-transitory computer-readable storage medium of claim 9, wherein the healthcare data comprises financial data.

13. At least one non-transitory computer-readable storage medium having instructions encoded thereon that, when executed by at least one computer processor, cause the at least one computer processor to perform a method comprising:

receiving healthcare data comprising electronic healthcare records associated with a plurality of patients of a healthcare professional, the plurality of patients comprising a first patient and a second patient;

preparing the electronic healthcare records with a consistent computer data structure configured for inputting to a trained statistical model, the electronic healthcare records including healthcare codes for the plurality of patients belonging to a plurality of different medical classification standards, wherein preparing the electronic healthcare records with the consistent computer data structure comprises:

transforming, by the at least one computer processor, the electronic healthcare records, from a plurality of differently-structured data formats into the consistent computer data structure, wherein an operation to perform the transforming includes one or more of:

an aggregation operation configured to identify a plurality of entities associated with the electronic healthcare records of differently-structured data formats and compile a plurality of data feeds for the plurality of entities into a common consolidated entity;

a normalization operation configured to reduce data redundancy across the plurality of data feeds for the plurality of entities; or an enrichment operation configured to identify and add curated electronic healthcare records of the plurality of differently-structured data formats from the plurality of data feeds for the plurality of entities, into a record formatted according to the consistent computer data structure;

validating, by the at least one computer processor, that the electronic healthcare records conform to the consistent computer data structure, wherein the consistent computer data structure is configured for use with at least one of a foundational concept data operation, a knowledge data operation, a service data operation, a clinical decision support data operation, a documentation data operation, an analytics data operation, or an administrative data operation;

inputting to the trained statistical model, the electronic healthcare records prepared with the consistent computer data structure, wherein the trained statistical model is trained on training data comprising, for each diagnosis of a plurality of diagnoses:

a respective variable; and linked with the respective variable, a set of healthcare codes corresponding to each medical classification standard of the plurality of different medical classification standards, wherein:

each healthcare code of the set of healthcare codes corresponds to the diagnosis;

surfacing, by the at least one computer processor, using the trained statistical model, at least one hidden relationship between the electronic healthcare records with the consistent computer data structure and at least one clinical intervention and encoding the at least one hidden relationship as an explicit value in the consistent computer data structure;

generating a workflow of the healthcare professional using an output of the trained statistical model calculated based on the electronic healthcare records prepared with the consistent computer data structure, the output of the trained statistical model comprising the at least one hidden relationship between the electronic healthcare records with the consistent computer data structure and the at least one clinical intervention;

generating a graphical user interface (GUI) representing the workflow of the healthcare professional;

providing the GUI representing the workflow of the healthcare professional to a display, wherein the GUI representing the workflow of the healthcare professional comprises:

one ordered list of a plurality of GUI elements representing the workflow prompting the healthcare professional to provide care to the first patient and provide care to the second patient after providing care to the first patient and comprising a respective plurality of healthcare events for the healthcare professional; and within the one ordered list, a first GUI element representing a first healthcare event specific to the first patient and a second GUI element representing a second healthcare event specific to the second patient, the first GUI element and the second GUI element being ordered with respect to each other within the plurality of GUI elements representing the workflow, wherein:

the prompting to provide care to the second patient after providing care to the first patient is generated based on the surfaced at least one hidden relationship between the electronic healthcare records with the consistent computer data structure and the at least one clinical intervention and using the healthcare codes belonging to the plurality of different medical classification standards;

continuously updating the workflow of the healthcare professional based on subsequent outputs of the trained statistical model calculated based on the electronic healthcare records prepared with the consistent computer data structure and based on updated healthcare codes for the plurality of patients belonging to the plurality of different medical classification standards; and automatically moving, based on the continuously updated workflow of the healthcare professional, positions, within the GUI, of the plurality of GUI elements representing the respective healthcare events, to provide the healthcare professional with continuously updated prompts to interact with the plurality of patients.

14. The at least one non-transitory computer-readable storage medium of claim 13, wherein ordering the list of the plurality of GUI elements representing the respective plurality of healthcare events using the output of the trained statistical model comprises:

formatting the first GUI element representing the first healthcare event of the plurality of GUI elements representing the plurality of healthcare events to include one or more visual indicators of priority, urgency, or severity.

15. The at least one non-transitory computer-readable storage medium of claim 13, wherein the ordered list of the plurality of GUI elements comprises at least one of a GUI element representing a task, a GUI element representing an alert, or a GUI element representing an appointment request for the healthcare professional.

16. The at least one non-transitory computer-readable storage medium of claim 13, wherein the GUI representing the workflow of the healthcare professional comprises a GUI element prompting the healthcare professional to follow up with the first patient.

17. The at least one non-transitory computer-readable storage medium of claim 13, wherein the GUI representing the workflow of the healthcare professional comprises, in the first GUI element representing the first healthcare event of the plurality of GUI elements representing the plurality of healthcare events, an indication of the first patient, that when selected, provides, to the healthcare professional, a GUI element representing a profile of the first patient.

18. The at least one non-transitory computer-readable storage medium of claim 13, wherein the GUI representing the workflow of the healthcare professional comprises, in the first GUI element representing the first healthcare event of the plurality of GUI elements representing the plurality of healthcare events, one or more visual indicators of priority, urgency, or severity.

19. The method of claim 1, wherein:
the trained statistical model is trained to:
receive the healthcare codes corresponding to the plurality of different medical classification standards, as an input; and
generate the plurality of healthcare events, based on the healthcare codes of the plurality of different medical classification standards, as an output.

* * * * *